United States Patent
Burcelin et al.

(10) Patent No.: US 11,285,180 B2
(45) Date of Patent: Mar. 29, 2022

(54) METHODS OF ENHANCING THE POTENCY OF INCRETIN-BASED DRUGS IN SUBJECTS IN NEED THEREOF

(71) Applicants: INSERM (INSTITUT NATIONAL DE LA SANTE ET DE LA RECHERCHE MEDICALE), Paris (FR); UNIVERSITY PAUL SABATIER TOULOUSE III, Toulouse (FR)

(72) Inventors: Remy Burcelin, Toulouse (FR); Francois Terce, Toulouse (FR); Estelle Grasset, Toulouse (FR); Jeffrey Christensen, Toulouse (FR); Xavier Collet, Toulouse (FR)

(73) Assignees: INSERM (Institut National de la Sante et de la Recherche Medicale), Paris (FR); Université Paul Sabatier Toulouse III, Toulouse (FR)

( * ) Notice: Subject to any disclaimer, the term of this patent is extended or adjusted under 35 U.S.C. 154(b) by 63 days.

(21) Appl. No.: 16/465,320

(22) PCT Filed: Dec. 5, 2017

(86) PCT No.: PCT/EP2017/081445
§ 371 (c)(1),
(2) Date: May 30, 2019

(87) PCT Pub. No.: WO2018/104263
PCT Pub. Date: Jun. 14, 2018

(65) Prior Publication Data
US 2019/0388486 A1    Dec. 26, 2019

(30) Foreign Application Priority Data

Dec. 6, 2016 (EP) .................................... 16306623

(51) Int. Cl.
| | | |
|---|---|---|
| *A61K 35/747* | (2015.01) | |
| *A23L 33/135* | (2016.01) | |
| *A61P 5/48* | (2006.01) | |
| *A61P 3/08* | (2006.01) | |
| *A61P 3/04* | (2006.01) | |
| *A61K 9/00* | (2006.01) | |
| *A61K 45/06* | (2006.01) | |

(52) U.S. Cl.
CPC .......... *A61K 35/747* (2013.01); *A23L 33/135* (2016.08); *A61K 9/0019* (2013.01); *A61P 3/04* (2018.01); *A61P 3/08* (2018.01); *A61P 5/48* (2018.01); *A61K 45/06* (2013.01)

(58) Field of Classification Search
CPC ....... A61K 35/747; A23L 33/135; A61P 5/48; A61P 5/50; A16P 3/08; A16P 3/10
See application file for complete search history.

(56) References Cited

U.S. PATENT DOCUMENTS

| | | | | | |
|---|---|---|---|---|---|
| 2012/0107291 A1* | 5/2012 | Burcelin | ............... | A61K 31/715 | |
| | | | | | 424/93.45 |
| 2015/0352189 A1* | 12/2015 | Schentag | ........... | G01N 33/5082 | |
| | | | | | 424/472 |

FOREIGN PATENT DOCUMENTS

WO    2010/146568 A2    12/2010

OTHER PUBLICATIONS

McCormack, Exenatide twice daily: a review of its use in the management of patients with Type 2 diabetes mellitus, Drugs, vol. 72, p. 325-351 (Year: 2014).*
Hussar, https://www.nursingcenter.com/ce_articleprint?an=00152193-201510000-00010 , New Drugs, p. 1-13 (Year: 2015).*
Al-Salami et al., Probiotic treatment reduces blood glucose levels and increases systemic absorption of gliclazide in diabetic rats, European Journal of Drug Metabolism and Pharmacokinetics, vol. 33, No. 2, pp. 101-106 (Year: 2008).*
Tian et al: "antidiabetic (type 2) effects of Lactobacillus G15 and Q14 in rats through regulation of intestinal permeability and microbiota", Food & Function, vo. 7, No. 9, pp. 3789-3797, Jan. 1, 2016.
Lin et al: "Oral Delivery of Pentameric Glucagon-Like Peptide-1 by Recombinant Lactobacillus in Diabetic Rats", Plos One, vol. 11, No. 9, p. e0162733, Sep. 9, 2016.
Alisi et al: "Randomised clinical trial: the beneficial effects of VSL#3 in obese children with non-alcoholic steatohepatitis", Alimentary Pharmacology & THERAPEUTICS., vol. 39, No. 11, pp. 1276-1285, Apr. 16, 2014.
Nutr et al: "3 Improvement in glucose telerance and insulin senstivity by probiotic strains of Indian gut origin in high-fat diet-fed C57BL/6J mice", Springer online, pp. 1-17, Oct. 18, 2016.

(Continued)

*Primary Examiner* — Taeyoon Kim
*Assistant Examiner* — Tiffany M Gough
(74) *Attorney, Agent, or Firm* — WCF IP

(57) ABSTRACT

The present invention relates to methods of enhancing the potency of incretin-based drugs in subjects in need thereof. Through different animal models, the inventors identified that a specific gut microbiota signature impairs GLP-1-activated gut-brain axis which could be transferred to germ free mice. The dysbiotic gut microbiota induces enteric neuropathy, reduces GLP-1 receptor and nNOS mRNA concentration, GLP-1-induced nitric oxide production for the control of insulin secretion and gastric emptying. The frequency of *Lactobacilli* in the ileum microbiota was tightly correlated with nMOS mRNA concentration, which is a mode of action of GLP-1, of the enteric nervous system opening a novel route for the improvement of GLP-1 based therapies in type 2 diabetic patients. In particular, the present invention relates to a method of enhancing the potency of an incretin-based drug administered to a diabetic subject as part of a treatment regimen.

8 Claims, 3 Drawing Sheets

(56) References Cited

OTHER PUBLICATIONS

Figure 1A:
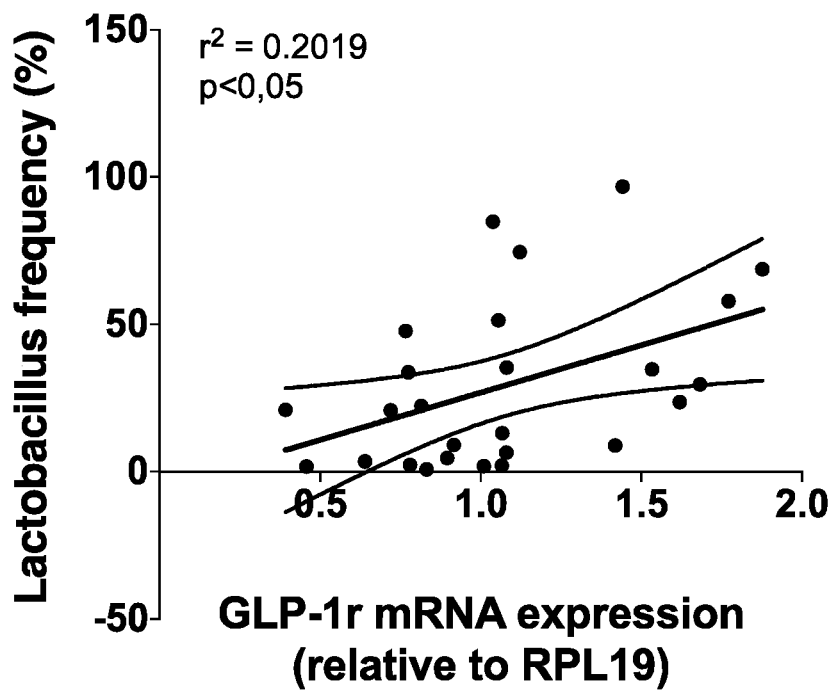

Simon et al: "Intake of Lactobacillus reuteri Improves Incretin and Insulin Secretion in Glucose-Tolerant Humans: A Proof of Concept", Diabetes Care, vol. 38, No. 10, pp. 1827-1834, Jun. 17, 2015.
Sato et al: "Gut Dysbiosis and Detection of "Live Gut Bacteria" in Blood of Japanese Patients With Type 2 Diabetes", Diabetes Care, vol. 37, No. 8, pp. 2343-2350, May 13, 2014.
Stenman et al: "Probiotic B420 and prebiotic polydextrose improve efficacy of antidiabetic drugs in mice", Diabetology & Metabolic Syndrome, vol. 7, No. 1, pp. 1-9, Sep. 12, 2015.
Yan et al: "Microflora Disturbance during Progression of Glucose Intolerance and Effect of Sitagliptin: An Animal Study", Journal of Diabetes Research, vol. 2016, pp. 1-10, Jan. 1, 2016.

* cited by examiner

METHODS OF ENHANCING THE POTENCY OF INCRETIN-BASED DRUGS IN SUBJECTS IN NEED THEREOF

FIELD OF THE INVENTION

The present invention relates to methods of enhancing the potency of incretin-based drugs in subjects in need thereof.

BACKGROUND OF THE INVENTION

The Glucagon Like Peptide-one (GLP-1) is an insulinotropic hormone secreted by enteroendocrine L cells in response to a meal. The hormone plays a key role on the glucose control since it regulates insulin and glucagon secretion, gastric emptying, food intake and blood flow to cite a few (Hoist, 2007). Two modes of action co-exist to explain these physiological actions. The first one involves paracrine action of GLP-1 secreted by intestinal L-cells which binds locally to GLP-1 receptors expressed by the enteric and vagus nerves (Richards et al., 2014). Through the triggering of the gut-brain-periphery axis the enteric hormonal signal is transmitted to the brain. The latter organ then redistributes the neuro-hormonal message to peripheral tissues that engages numerous physiological functions involve in the control of glucose homeostasis (Burcelin et al., 2009). The second mode of action is endocrine where blood GLP-1 triggers receptors expressed by distant cells notably the beta cells from the Langerhans islets (Richards et al., 2014), to cite the most studied one (Drucker et al., 1987; Farilla et al., 2003). The respective contribution of both pathways on the control of glycemia is unknown and could vary according to the physiology of each individual. G proteins, adenylate cyclase, cAMP, EPAC, PKA, CREB, PKC, Akt, ERK, nitric oxide (NO), and NO synthase (NOS) are the main signaling molecules responsible for GLP-1 intracellular signaling and action (Cabou et al., 2011; Ding and Zhang, 2012; Drucker et al., 1987; Farilla et al., 2003; Han et al., 2012; Liu et al., 2015; Pujadas et al., 2015; Rotondo et al., 2011). Similarly, the contribution of signaling molecule on the triggering of a GLP-1-dependent function is not known but could follow the rule of individual diversity leading to different sensitivity to GLP-1. The insulinotropic action of the native GLP-1 has been the basis for strategies aiming at treating type 2 diabetes (T2D). However, the active peptide GLP-17-37 is rapidly degraded by the dipeptidyl peptidase 4 (DPP4), an amino-terminal peptidase largely distributed throughout the gut, into an inactive GLP-$1_{9-37}$ peptide (Hansen et al., 1999). To overcome this issue, two pharmacological strategies have been elaborated and are currently been used. The first one involves the use of different GLP-1 agonists resistant to the DPP4, while for the second one DPP4 inhibitors have been developed (Dalle et al., 2013). Both aim at increasing the circulating concentration of intact GLP-1 and of the corresponding receptor agonists to magnify the GLP-1 receptor signaling and the corresponding physiological functions. However, clinical evidences show that 40-65% of T2D patients fail to reach in response to GLP-1-based therapies i.e. HbAlc lower than 6.5% (Esposito et al., 2011). This observation suggests that the efficacy of GLP-1-based therapies depends upon the patient. Therefore, a difference in GLP-1 action could be suspected defining various GLP-1 sensitivities and states of unresponsiveness. This issue is of importance from both therapeutic and mechanistic points of view. The causes and mechanisms responsible for the impaired GLP-1 sensitivity in subsets of T2D patients could be linked to the multifactorial origin of the disease. For instance, the lipo-glucotoxicity characterizing some T2D patients could hamper the efficacy of GLP-1r agonist to trigger glucose-induced insulin secretion, notably through a down-regulation of the GLP-1r gene expression (Duca et al., 2015; Hodson et al., 2013; Pujadas et al., 2015; Ten Kulve et al., 2015; Xu et al., 2007; Yang et al., 2016; Younan and Rashed, 2007). Furthermore, autonomic neuropathy (Anitha et al., 2006; Lee et al., 2012; Stenkamp-Strahm et al., 2013) could reduce the gut-brain axis hampering numerous GLP-1 dependent physiological functions (Lobinet et al., 2015). A more recent hypothesis concerns the importance of gut microbiota dysbiosis in the development of metabolic diseases (Backhed et al., 2004; Gill et al., 2006; Ley et al., 2005). The mechanisms discovered so far involve microbial-produced factors such as lipopolysaccharides (LPS), peptidoglycans, short chain fatty acids (SCFA), and secondary bile acids. Regarding bacterial recognition mechanisms microbial molecular pattern receptors TLRs and NLRs have been described as important for the glycemic control (Cani et al., 2007a; Cani et al., 2008; Denou et al., 2015; Prajapati et al., 2014) and could therefore be involved in the mechanisms responsible for the GLP-1 physiology. GLP-1 homeostasis and gut microbiota are tightly linked. Recent evidences show that germ free mice are characterized by extremely high plasma GLP-1 concentrations whereas plasma insulin concentration remains low (Wichmann et al., 2013). LPS, SCFA and indole signaling control GLP-1 secretion (Cani et al., 2007b; Chimerel et al., 2014; Nguyen et al., 2014; Tolhurst et al., 2012). Recent evidence show that gut microbiota dysbiosis produces acetate which impairs the parasympathetic nervous system leading to an alteration of the gut-brain axis towards the development of metabolic syndrome (Perry et al., 2016). In addition, propionate and butyrate productions by gut microbiota activate intestinal gluconeogenesis that transmits, through the gut-brain axis the intestinal signal for the control of food intake and glycemia (De Vadder et al., 2014). Altogether, gut microbiota dysbiosis, such as characterized in type 2 diabetic patients and in rodents (Forslund et al., 2015; Garidou et al., 2015; Qin et al., 2012; Sato et al., 2014), could control GLP-1 responsiveness and the corresponding physiological function such as the gut-brain mediated insulin secretion.

SUMMARY OF THE INVENTION

The present invention relates to methods of enhancing the potency of incretin-based drugs in subjects in need thereof. In particular, the present invention is defined by the claims.

DETAILED DESCRIPTION OF THE INVENTION

GLP-1 based therapies control glycemia in type 2 diabetic patients. However, in some patients the corresponding efficiency is reduced so that the treatment has to be discontinued defining a state of GLP-1 unresponsiveness. Through different animal models, the inventors identified that a specific gut microbiota signature impairs GLP-1-activated gut-brain axis which could be transferred to germ free mice. The dysbiotic gut microbiota induces enteric neuropathy, reduces GLP-1 receptor and nNOS mRNA concentration, GLP-1-induced nitric oxide production for the control of insulin secretion and gastric emptying. The frequency of *Lactobacilli* in the ileum microbiota was tightly correlated with nMOS mRNA concentration, which is a mode of action of GLP-1, of the enteric nervous system opening a novel route for the improvement of GLP-1 based therapies in type 2 diabetic patients.

Accordingly the first object of the present invention relates to a method of restoring the incretin effect in a subject in need thereof comprising an effective amount of at least one *Lactobacillus* probiotic strain.

As used herein, the term "incretins" has its general meaning in the art and refers to a group of metabolic hormones that stimulate a decrease in blood glucose levels (i.e. "incretin effect"). Incretins are released after eating and augment the secretion of insulin released from pancreatic beta cells of the islets of Langerhans by a blood glucose-dependent mechanism. They also slow the rate of absorption of nutrients into the blood stream by reducing gastric emptying and may directly reduce food intake. They also inhibit glucagon release from the alpha cells of the islets of Langerhans. The two main incretin hormone are the intestinal peptides glucagon-like peptide-1 (GLP-1) and gastric inhibitory peptide (also known as: glucose-dependent insulinotropic polypeptide or GIP).

As used herein, the expression "incretin effect" refers to the effect mediated by the release of incretin in response to oral nutrient administration which leads to the insulin secretion.

As used herein, to "restore," for example, with respect to the incretin effect, suitably includes enhancing, potentiating, increasing, reestablishing, re-activating, or improving the physiological state. For example, a subject having Type 2 diabetes may exhibit diminished or even zero incretin effect, i.e., diminished or no activity of incretin, or diminished or no increase in insulin secretion upon nutrient administration. Consequently, to "restore" the incretin effect suitably increases, though does not necessarily normalize, incretin activity or insulin secretion upon nutrient administration in a subject.

In some embodiments, the method of the present invention is particularly suitable for restoring the incretin effect of GLP-1. As used herein, the term "GLP-1" has its general meaning in the art and refers the Glucagon-like peptide-1 (GLP-1) which is a neuropeptide and an incretin derived from the transcription product of the proglucagon gene. Human GLP-1 is a 37 amino acid residue peptide originating from preproglucagon which is synthesised i.a. in the L-cells in the distal ileum, in the pancreas and in the brain. GLP-1 is an important gut hormone with regulatory function in glucose metabolism and gastrointestinal secretion and metabolism. Processing of preproglucagon to give GLP-1 (7-36)-amide, GLP-1(7-37) and GLP-2 occurs mainly in the L-cells. The fragments GLP-1(7-36)-amide and GLP-1(7-37) are both glucose-dependent insulinotropic agents.

In some embodiments, the method of the present invention is particularly suitable for restoring the incretin effect of GIP. As used herein, the term "GIP"

In some embodiments, the subject is suitably a mammal, such as a human, dog, cat, primate, etc.

In some embodiments, the subject suffers from type 2 diabetes. As used herein, the term "type 2 diabetes" refers to a condition characterized by excess glucose production in spite of the availability of insulin, and circulating glucose levels remain excessively high as a result of inadequate glucose clearance. In some embodiments, the diabetic subject suffers from overweight or obesity. Overweight may be defined as the condition wherein the individual has a body mass index (BMI) greater than or 25 kg/m$^2$ and less than 30 kg/m$^2$. The terms "overweight" and "pre-obese" are used interchangeably. Obesity may be defined as the condition wherein the individual has a BMI equal to or greater than 30 kg/m$^2$. According to a WHO definition the term obesity may be categorized as follows: class I obesity is the condition wherein the BMI is equal to or greater than 30 kg/m$^2$ but lower than 35 kg/m$^2$; class II obesity is the condition wherein the BMI is equal to or greater than 35 kg/m$^2$ but lower than 40 kg/m$^2$; class III obesity is the condition wherein the BMI is equal to or greater than 40 kg/m$^2$. Obesity may include e.g. visceral or abdominal obesity. Visceral obesity may be defined as the condition wherein a waist-to-hip ratio of greater than or equal to 1.0 in men and 0.8 in women is measured. It defines the risk for insulin resistance and the development of pre-diabetes. Abdominal obesity may usually be defined as the condition wherein the waist circumference is >40 inches or 102 cm in men, and is >35 inches or 94 cm in women. With regard to a Japanese ethnicity or Japanese patients abdominal obesity may be defined as waist circumference ≥85 cm in men and ≥90 cm in women (see e.g. investigating committee for the diagnosis of metabolic syndrome in Japan).

In some embodiments, the subject suffers from type 1 diabetes. As used herein, the term "Type 1 diabetes" (also referred to as insulin-dependent, juvenile diabetes, or childhood-onset diabetes), refers to an autoimmune disease that results in destruction of insulin-producing beta cells of the pancreas, eventually resulting in a lack of insulin production.

The method of the present invention is particularly suitable for the treatment of subjects who do not achieve adequate glycemic control following the administration of an incretin-based drug.

Accordingly a further object of the present invention relates to a method of enhancing the potency of an incretin-based drug administered to a diabetic subject as part of a treatment regimen, the method comprising administering to the subject a pharmaceutically effective amount of at least one *Lactobacillus* probiotic strain in combination with the incretin-based drug.

As used herein, the term "incretin-based drug" has its general meaning in the art and refers to any compound or composition (e.g. food composition) capable of acting as incretin receptor agonists, inhibiting the proteolytic degradation of incretins or stimulating the secretion of incretins. In particular, incretin-based drugs refer to the class of drugs comprising GLP-1 receptor agonists and DDP-4 inhibitors. Additionally incretin-based drug also include GIP receptor agonist, dual GLP-1/GIP receptor agonists and triple GLP-1/GIP/glucagon receptor agonists.

As used herein, the term "GLP-1 receptor agonist" has its general meaning in the art and refers to any compound, including peptides and non-peptide compounds, which fully or partially activates the human GLP-1 receptor. In some embodiments, the "GLP-1 receptor agonist" is any peptide or non-peptide molecule that binds to a GLP-1 receptor with an affinity constant (KD) or a potency (EC50) below 1 µM, such as below 100 nM as measured by methods known in the art (see WO 98/08871, which is incorporated herein in its entirety) and exhibits insulinotropic activity, where insulinotropic activity may be measured using in vivo or in vitro assays known to those skilled in the art. Examples of GLP-1 receptor agonists include exendins, exendin analogs, exendin agonists, GLP-1 (7-37), GLP-1 (7-37) analogs, GLP-1 (7-37) agonists, and the like. The term "exendin" includes naturally occurring (or synthetic versions of naturally occurring) exendin peptides that are found in the salivary secretions of the Gila monster (*Heloderma suspectum*). Exendins of particular interest include exendin-3 and exendin-4. The exendins, exendin analogs, and exendin agonists for use in the methods described herein may optionally be amidated, and may also be in an acid form, pharmaceutically acceptable salt form, or any other physiologically active form of the molecule. Exendin-4 is a 39 amino acid residue peptide isolated from the venom of *Heloderma horridum*, and this peptide shares 52% homology with GLP-1. Synthetic exendin-4, also known as exenatide, is commercially available as BYETTA® (Amylin Pharmaceuticals, Inc. and Eli Lilly and Company). BYETTA® contains exenatide, a preservative (e.g., metacresol), a tonicity-adjusting agent (e.g., mannitol), and a buffer (e.g., an acetate buffer). A once weekly formulation of exenatide is currently in development and is described in WO 2005102293, the disclosure of which is incorporated by reference herein. This once weekly formulation comprises exenatide and biodegradable polymeric (e.g., poly(lactide-co-glycolide)) microspheres, and is referred to herein as EQW or BYDUREON™ (Amylin Pharmaceuticals, Inc., Eli Lilly and Company, Alkermes, Inc.). Examples of exendins and exendin analogs useful in the methods described herein include those described in WO 9805351; WO 9907404; WO 9925727; WO 9925728; WO 9940788; WO 0041546; WO 0041548; WO 0073331; WO 0151078; WO 03099314; U.S. Pat. Nos. 6,956,026; 6,506,724; 6,703,359; 6,858,576; 6,872,700; 6,902,744; 7,157,555; 7,223,725; 7,220,721; US Publication No. 20030036504; and US Publication No. 20060094652, the disclosures of which are incorporated by reference herein in their entirety. As used herein, "GLP-1(7-37) analogs" refers to peptides or other compounds which elicit a biological activity similar to that of GLP-1(7-37), when evaluated by art-known measures such as receptor binding assays or in vivo blood glucose assays as described, e.g., by Hargrove et al, Regulatory Peptides, 141:113-119 (2007), the disclosure of which is incorporated by reference herein. In one embodiment, the term "GLP-1(7-37) analog" refers to a peptide that has an amino acid sequence with 1, 2, 3, 4, 5, 6, 7 or 8 amino acid substitutions, insertions, deletions, or a combination of two or more thereof, when compared to the amino acid sequence of GLP-1(7-37). In one embodiment, the term "GLP-1(7-37)" refers to a peptide having at least 75% sequence identity to GLP-1(7-37). In other embodiments, the term "GLP-1(7-37) analog" refers to peptides having at least 80% sequence identity to GLP-1(7-37); at least 85% sequence identity to GLP-1(7-37); at least 90% sequence identity to GLP-1(7-37); or at least 95% sequence identity to GLP-1(7-37). Exemplary GLP-1(7-37) and GLP-1(7-37) analogs include GLP-1(7-37) (SEQ ID NO:22); GLP-1(7-36))-NH2 (SEQ ID NO:23); liraglutide (VICTOZA® from Novo Nordisk); albiglutide (SYNCRIA® from GlaxoSmithKline); taspoglutide (Hoffman La-Roche); LY2189265 (Eli Lilly and Company); and LY2428757 (Eli Lilly and Company). In some embodiments, the GLP-1(7-37) or GLP-1(7-37) analogs are covalently linked (directly or by a linking group) to an Fc portion of an immunoglobulin (e.g., IgG, IgE, IgG, and the like). In some embodiments, the GLP-1(7-37) or GLP-1(7-37) analog may be covalently linked (directly or through a linking group) to one or two polyethylene glycol molecules. In one embodiment, the GLP-1 receptor agonist is semaglutide.

As used herein, the term "DPP-4" has its general meaning in the art and refers to the dipeptidyl peptidase IV enzyme also known as CD26 which is a serine protease known to lead to the cleavage of a dipeptide from the N-terminal end of a number of proteins having at their N-terminal end a prolin or alanin residue. Accordingly, the term "DPP-4 inhibitor" has its general meaning in the art and refers to a compound that exhibits inhibitory activity on the enzyme dipeptidyl peptidase IV (DPP-4). The inhibitory effect on DPP-4 can be determined by methods known in the literature, in particular as described in the application WO 02/068420 or WO 2004/018468, which are incorporated herein by reference in its entirety. Due to this property DPP-4 inhibitors interfere with the plasma level of bioactive peptides including GLP-1 and represent drugs for the treatment of diabetes mellitus. DDP-4 inhibitors are well known in the art. For example, DPP-4 inhibitors and their uses are disclosed in WO 2002/068420, WO 2004/018467, WO 2004/018468, WO 2004/018469, WO 2004/041820, WO 2004/046148, WO 2005/051950, WO 2005/082906, WO 2005/063750, WO 2005/085246, WO 2006/027204, WO 2006/029769, WO2007/014886; WO 2004/050658, WO 2004/111051, WO 2005/058901, WO 2005/097798; WO 2006/068163, WO 2007/071738, WO 2008/017670; WO 2007/128721, WO 2007/128724, WO 2007/128761, or WO 2009/121945. A non-exhaustive list of DPP-4 Inhibitors comprises the molecules that are identified in the literature as Sitagliptin, Vildagliptin, Saxagliptin, Alogliptin, Carmegliptin, Gosogliptin, Tenegliptin, Retagliptin, Linagliptin, Melogliptin, DA-1229, ABN-279, AMG-222, PSN-9301, P32/98, LC-150444, LC-150033, TAK-100, SYR-322, SYR-472/TAK-472, CWP-0403, KRP-104, Sulphostin, or their pharmaceutically acceptable salts. According to a particular embodiment of the invention, the DPP-4 Inhibitor is selected in the group consisting of Sitagliptin, Vildagliptin, Saxagliptin, Alogliptin and the pharmaceutically acceptable salts thereof.

As used herein, the term "GIP receptor agonist" refers to a compound in particular a peptide that binds to and activates downstream signaling of the GIP receptor.

As used herein, the term "dual GLP-1/GIP receptor agonist" refers to a molecule, in particular a peptide that is capable of binding to both receptors of GLP-1 and GIP and thus activate downstream signaling of the receptors. Examples of dual GLP-1/GIP receptor agonists are described in patent applications WO 2011/119657, WO 2012/138941, WO 2010/011439, WO 2010/148089, WO 2011/094337, WO 2012/088116, WO 2013/164483, WO 2014/192284 WO2015086729 and WO2016111971 the contents of which are herein incorporated by reference. Other examples are described in Frias J P, Bastyr E J 3rd, Vignati L, Tschop M H, Schmitt C, Owen K, Christensen R H, DiMarchi R D. The Sustained Effects of a Dual GIP/GLP-1 Receptor Agonist, NNC0090-2746, in Patients with Type 2 Diabetes. Cell Metab. 2017 Aug. 1; 26(2):343-352.e2. doi: 10.1016/j.cmet.2017.07.011.

1: Portron A, Jadidi S, Sarkar N, DiMarchi R, Schmitt C. Pharmacodynamics, pharmacokinetics, safety and tolerability of the novel dual glucose-dependent insulinotropic polypeptide/glucagon-like peptide-1 agonist RG7697 after single subcutaneous administration in healthy subjects. Diabetes Obes Metab. 2017 October; 19(10):1446-1453. doi: 10.1111/dom.13025. Epub 2017 Jul. 25. PubMedPMID: 28741871.

2: Schmitt C, Portron A, Jadidi S, Sarkar N, DiMarchi R. Pharmacodynamics, pharmacokinetics and safety of multiple ascending doses of the novel dual glucose-dependent insulinotropic polypeptide/glucagon-like peptide-1 agonist RG7697 in people with type 2 diabetes mellitus. Diabetes Obes Metab. 2017 October; 19(10):1436-1445. doi: 10.1111/dom.13024. Epub 2017 Jul. 20. PubMedPMID: 28730694.

3: Norregaard P K, Deryabina M A, Tofteng Shelton P, Fog J U, Daugaard J R, Eriksson P O, Larsen L F, Jessen L. A novel GIP analogue, ZP4165, enhances glucagon-like peptide-1-induced body weight loss and improves glycaemic control in rodents. Diabetes Obes Metab. 2017 Jun. 9. doi: 10.1111/dom.13034. [Epub ahead of print] PubMed PMID: 28598027.

4: Shi L, Zhang Z, Li L, Holscher C. A novel dual GLP-1/GIP receptor agonist alleviates cognitive decline by re-sensitizing insulin signaling in the Alzheimer icy. STZ rat model. Behav Brain Res. 2017 Jun. 1; 327:65-74. doi: 10.1016/j.bbr.2017.03.032. Epub 2017 Mar. 23. PubMed PMID: 28342971.

5: Yuan Z, Li D, Feng P, Xue G, Ji C, Li G, Holscher C. A novel GLP-1/GIP dual agonist is more effective than liraglutide in reducing inflammation and enhancing GDNF release in the MPTP mouse model of Parkinson's disease. Eur J Pharmacol. 2017 Oct. 5; 812:82-90. doi: 10.1016/j.ejphar.2017.06.029. Epub 2017 Jun. 27. PubMed PMID: 28666800.

6: Moran B M, McKillop A M, O'Harte F P. Development of novel ligands for peptide GPCRs. Curr Opin Pharmacol. 2016 December; 31:57-62. doi: 10.1016/j.coph.2016.08.009. Epub 2016 Sep. 5. Review. PubMed PMID: 27607913.

7: Cao L, Li D, Feng P, Li L, Xue G F, Li G, Holscher C. A novel dual GLP-1 and GIP incretin receptor agonist is neuroprotective in a mouse model of Parkinson's disease by reducing chronic inflammation in the brain. Neuroreport. 2016 Apr. 13; 27(6):384-91. doi: 10.1097/WNR.0000000000000548. PubMed PMID: 26918675.

As used herein, the term "triple GLP-1/GIP/glucagon receptor agonists" refers to a molecule, in particular a peptide that is capable of binding to both receptors of GLP-1, GIP and glucagon and thus activate downstream signaling of the receptors. Examples of triple GLP-1/GIP/glucagon receptor agonists are described in:

Neuroprotective effects of a triple GLP-1/GIP/glucagon receptor agonist in the APP/PS1 transgenic mouse model of Alzheimer's disease. JingjingTai et al. Brain research, Volume 1678, 1 Jan. 2018, Pages 64-74;

A novel GLP-1/glucagon hybrid peptide with triple-acting agonist activity at GIP, GLP-1 and glucagon receptors and therapeutic potential in high-fat fed mice. Victor A. Gault et al. J. Biol. Chem. 288, 35581-35591 (2013); Patent application WO2015/067716.

As used herein, the expressions "enhancing the potency of an incretin-based drug" refers to the ability of the *Lactobacillus* probiotic strain to increase the ability of the incretin-based drug to decrease hyperinsulinemia.

A further object of the present invention relates to a method of treating type 2 diabetes in a subject in need thereof comprising administering to the subject a therapeutically effective combination of at least one *Lactobacillus* probiotic strain and an incretin-based drug, wherein administration of the combination results in enhanced therapeutic efficacy relative to the administration of the incretin-based drug alone.

A further object of the present invention relates to a method of treating type 1 diabetes in a subject in need thereof comprising administering to the subject a therapeutically effective combination of at least one *Lactobacillus* probiotic strain and an incretin-based drug, wherein administration of the combination results in enhanced therapeutic efficacy relative to the administration of the incretin-based drug alone.

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., pain, disease manifestation, etc.]).

The method is particularly suitable for preventing the complications of diabetes. As used herein, the term "complications of diabetes" includes cardiometabolic complications, metabolic complications, hepatic complications, respiratory complications, renal complications, nervous system complications and inflammation complications. Cardiometabolic complications encompasses cardiovascular and metabolic complications of diabetes and/or obesity. Metabolic complications of diabetes include diabetic ketoacidosis, hyperosmolar non-ketotic coma, lactic acidosis, hypoglycemia and dyslipidemia. Cardiovascular complications of diabetes include hypertension, cardiovascular disease (CVD) and brain ischemia, atherosclerosis and heart failure. Hepatic complications of diabetes include fatty liver, hepatic steatosis, liver fibrosis, cirrhosis and hepatocarcinoma. Nervous system complications include neuropathy and retinopathies and neurodegenerative diseases. Inflammation complications typically include arthritis.

As used the terms "combination" and "combination therapy" are interchangeable and refer to treatments comprising the administration of at least two compounds administered simultaneously, separately or sequentially. As used herein the term "co-administering" as used herein means a process whereby the combination of the incretin-based drug and the probiotic *Lactobacillus* strain, is administered to the same patient. The incretin-based drug and the probiotic *Lactobacillus* strain may be administered simultaneously, at essentially the same time, or sequentially. The incretin-based drug and the probiotic *Lactobacillus* strain can be administered separately by means of different vehicles or composition. The incretin-based drug and the probiotic *Lactobacillus* strain can also administered in the same vehicle or composition (e.g. pharmaceutical composition). The incretin-based drug and the probiotic *Lactobacillus* strain may be administered one or more times and the number of administrations of each component of the combination may be the same or different.

As used herein, the term "therapeutically effective combination" as used herein refers to an amount or dose of a incretin-based drug together with the amount or dose of the probiotic *Lactobacillus* strain that is sufficient to treat the disease (e.g. type 2 diabetes).The amount of the incretin-based drug in a given therapeutically effective combination may be different for different individuals, and will be dependent upon the one or more additional agents or treatments included in the combination. The "therapeutically effective amount" is determined using procedures routinely employed by those of skill in the art such that an "improved therapeutic outcome" results. It will be understood, however, that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidential with the specific polypeptide employed; and like factors well known in the medical arts. For example, it is well within the skill of the art to start doses of the compound at levels lower than those required to achieve the desired therapeutic effect and to gradually increase the dosage until the desired effect is achieved.

In some embodiments, the method of the present invention further comprises administering to the subject another drugs selected from the group consisting of sulfonylurea drugs, biguanides, alpha-glucosidase inhibitors, thiazolidinediones, and meglitinides. Sulfonylurea drugs reduce blood glucose levels by stimulating pancreatic beta cells to secrete insulin, which results in an elevated plasma insulin concentration, a secondary action is improvement in hepatic and peripheral insulin sensitivity (Webb, Lipsky et al. 2000; Takiya and Chawla 2002). Biguanides like Metformin (brand name Glucophage) lower blood glucose levels primarily by decreasing the amount of glucose produced by the liver; metformin also helps to lower blood glucose levels by making muscle tissue more sensitive to insulin (insulin sensitizer) so glucose can be absorbed (Webb, Lipsky et al.2000; Takiya and Chawla 2002). Alpha-glucosidase inhibitors such as acarbose (brand name Precose) and meglitol (brand name Glyset) decrease the absorption of carbohydrates from the digestive tract, thereby lowering the after-meal glucose levels; the principal action of alpha-glucosidase inhibitors is the partial inhibition of intestinal enzymes that break down carbohydrates into monosaccharides (Webb, Lipsky et al. 2000; Takiya and Chawla 2002). Thiazolidinediones such as rosiglitazone (brand name Avandia), troglitazone (brand name Rezulin), and pioglitazone (brand name ACTOS) increase the cell's sensitivity (responsiveness) to insulin and also reduce glucose production in the liver (Webb, Lipsky et al. 2000; Takiya and Chawla 2002). Meglitinides such as repaglinide (brand name Prandin) and nateglinide (brand name Starlix) stimulates the release of insulin from the pancreatic beta cells by closing ATP-sensitive potassium channels (Webb, Lipsky et al. 2000; Takiya and Chawla 2002).

A further object of the present invention relates to a method of preventing diabetes in a subject in need thereof comprising administering to the subject a therapeutically effective amount of at least one *Lactobacillus* probiotic strain.

A further object of the present invention relates to a method of preventing glucose intolerance in a subject in need thereof comprising administering to the subject a therapeutically effective amount of at least one *Lactobacillus* probiotic strain. The term "glucose intolerance" as used herein is defined as exceptional sensitivity to glucose. Glucose-intolerance is a pre-diabetic state of hyperglycemia that is associated with insulin resistance and increased risk of cardiovascular pathology.

A further object of the present invention relates to a method of improving glycemic management in a subject in need thereof comprising administering to the subject a therapeutically effective amount of at least one *Lactobacillus* probiotic strain.

As used herein, the term "improving glycemic management" should be understood to mean lowering plasma blood glucose levels, especially post-prandial blood glucose levels, treating or preventing hyperglycaemia, increasing post prandial insulin secretion, regulating glucose homeostasis, reducing insulin resistance.

Typically, the probiotic *Lactobacillus* strain of the present invention is administered to the subject by ingestion (i.e. oral route) and the incretin-based drug is administered to the subject subcutaneously.

As used herein, the term "*Lactobacillus*" refers to members of the genus *Lactobacillus*, in the family Lactobacillaceae. These bacteria are Gram-positive optionally anaerobic bacteria that represent a major part of the bacterial group often referred to as "lactic acid bacteria". The genus includes any of the following species: *Lactobacillus acetotolerans, Lactobacillus acidipiscis, Lactobacillus acidophilus, Lactobacillus agilis, Lactobacillus algidus, Lactobacillus alimentarius, Lactobacillus amylolyticus, Lactobacillus amylophilus, Lactobacillus amylovorus, Lactobacillus animalis, Lactobacillus arizonensis, Lactobacillus aviarius, Lactobacillus bifermentans, Lactobacillus brevis, Lactobacillus buchneri, Lactobacillus casei, Lactobacillus coelohominis, Lactobacillus collinoides, Lactobacillus coryniformis* subsp. *coryniformis, Lactobacillus coryniformis* subsp. *torquens, Lactobacillus crispatus, Lactobacillus curvatus, Lactobacillus cypricasei, Lactobacillus delbrueckii* subsp. *bulgaricus, Lactobacillus delbrueckii* subsp *delbrueckii, Lactobacillus delbrueckii* subsp. *lactis, Lactobacillus durianus, Lactobacillus equi, Lactobacillus farciminis, Lactobacillus ferintoshensis, Lactobacillus fermentum, Lactobacillus formicalis, Lactobacillus fructivorans, Lactobacillus frumenti, Lactobacillus fuchuensis, Lactobacillus gallinarum, Lactobacillus gasseri, Lactobacillus graminis, Lactobacillus hamsteri, Lactobacillus helveticus, Lactobacillus helveticus* subsp. *jugurti, Lactobacillus heterohiochii, Lactobacillus hilgardii, Lactobacillus homohiochii, Lactobacillus intestinalis, Lactobacillus japonicus, Lactobacillus jensenii, Lactobacillus johnsonii, Lactobacillus kefiri, Lactobacillus kimchii, Lactobacillus kunkeei, Lactobacillus leichmannii, Lactobacillus letivazi, Lactobacillus lindneri, Lactobacillus malefermentans, Lactobacillus mali, Lactobacillus maltaromicus, Lactobacillus manihotivorans, Lactobacillus mindensis, Lactobacillus mucosae, Lactobacillus murinus,*

*Lactobacillus nagelii, Lactobacillus oris, Lactobacillus panis, Lactobacillus pantheri, Lactobacillus parabuchneri,*

*Lactobacillus paracasei* subsp. *paracasei*, *Lactobacillus paracasei* subsp. *pseudoplantarum*, *Lactobacillus paracasei* subsp. *tolerans*, *Lactobacillus parakefiri*, *Lactobacillus paralimentarius*, *Lactobacillus paraplantarum*, *Lactobacillus pentosus*, *Lactobacillus perolens*, *Lactobacillus plantarum*, *Lactobacillus pontis*, *Lactobacillus psittaci*, *Lactobacillus reuteri*, *Lactobacillus rhamnosus*, *Lactobacillus ruminis*, *Lactobacillus sakei*, *Lactobacillus salivarius*, *Lactobacillus salivarius* subsp. *salicinius*, *Lactobacillus salivarius* subsp. *salivarius*, *Lactobacillus sanfranciscensis*, *Lactobacillus sharpeae*, *Lactobacillus suebicus*, *Lactobacillus thermophilus*, *Lactobacillus thermotolerans*, *Lactobacillus vaccinostercus*, *Lactobacillus vaginalis*, *Lactobacillus versmoldensis*, *Lactobacillus vitulinus*, *Lactobacillus vermiforme*, *Lactobacillus zeae*. Even more preferably, *Lactobacillus* strains are those selected from the group consisting of *Lactobacillus johnsonii* LaI NCC 2461 (CNCM 1-2116), *Lactobacillus reuterii* strains 4000 and 4020 (from BioGaia Biologics Inc., Raleigh, N.C.), *Lactobacillus paracasei* strains CNCM 1-1390, CNCM 1-1391, CNCM 1-1392, *Lactobacillus casei* strain Shirota, *Lactobacillus acidophilus* strain CNCM I-1447, *Lactobacillus acidophilus* Lat 11/83, *Lactobacillus acidophilus* NCC 2463 (=CNCM I-2623), *Lactobacillus rhamnosus* GG (ATCC 53103), *Lactobacillus rhamnosus* 271 (DSMZ 6594) and *Lactobacillus rhamnosus* VTT E-800.

As used herein the term "probiotic" is meant to designate live microorganisms which, they are integrated in a sufficient amount, exert a positive effect on health, comfort and wellness beyond traditional nutritional effects. Probiotic microorganisms have been defined as "Live microorganisms which when administered in adequate amounts confer a health benefit on the host" (FAO/WHO 2001). As used herein the expression "probiotic *Lactobacillus* strain" denotes a *Lactobacillus* strain that has a beneficial effect on the health and well-being of the host.

In some embodiments, the probiotic *Lactobacillus* strain of the present invention is a viable probiotic *Lactobacillus* strain. The expression "viable probiotic *Lactobacillus* strain" means a microorganism which is metabolically active and that is able to colonize the gastro-intestinal tract of the subject.

In some embodiments, the probiotic *Lactobacillus* strain of the present invention is a non-viable probiotic *Lactobacillus* strain consisting of a mixture of bacterial fragments. In some embodiments, the mixture of bacterial fragments of the present invention consists of proteins from the *Lactobacillus* strain. In some embodiments, the probiotic *Lactobacillus* strain of the present invention is selected from food grade bacteria. "Food grade bacteria" means bacteria that are used and generally regarded as safe for use in food.

Typically, the probiotic *Lactobacillus* strain of the present invention is produced with any appropriate culture medium well known in the art. Various fermentation media are suitable according to the invention, such as (but not limited to) e.g. firstly an industrial medium, in which the strain(s) is/are grown, and that is used as is or after concentration (e.g. drying) or after addition to another food base or product. Alternatively, bacterial cells, or bacterial cells with medium (e.g. the fermentation broth), or fractions of such cell comprising medium (i.e. medium with said bacterial strain/s) may be used. The cells or the cell comprising medium comprise live or viable bacterial cells and/or dead or non-viable bacterial cells of the strain(s). The medium may thus be treated by, but not limited to, heating or sonication. Also lyophilized, or frozen, bacteria and/or cell-free media (which may be concentrated) are encompassed in the methods for preparing the probiotic *Lactobacillus* strain of the present invention. In some embodiments, the probiotic *Lactobacillus* strain of the present invention is encapsulated in order to be protected against the stomach. Accordingly, in some embodiments the probiotic *Lactobacillus* strain of the present invention is formulated in compositions in an encapsulated form so as significantly to improve their survival time. In such a case, the presence of a capsule may in particular delay or prevent the degradation of the microorganism in the gastrointestinal tract. It will be appreciated that the compositions of the present embodiments can be encapsulated into an enterically-coated, time-released capsule or tablet. The enteric coating allows the capsule/tablet to remain intact (i.e., undissolved) as it passes through the gastrointestinal tract, until such time as it reaches the intestine. Methods of encapsulating live bacterial cells are well known in the art (see, e.g., U.S. patents to General Mills Inc. such as U.S. Pat. No. 6,723,358). For example, microencapsulation with alginate and Hi-Maize™ starch followed by freeze-drying has been proved successful in prolonging shelf-life of bacterial cells in dairy products [see, e.g., Kailasapathy et al. Curr Issues Intest Microbiol. 2002 September; 3(2):39-48]. Alternatively encapsulation can be done with glucomannane fibers such as those extracted from *Amorphophallus konjac*. Alternatively, entrapment of viable probiotic in sesame oil emulsions may also be used [see, e.g., Hou et al. J. Dairy Sci. 86:424-428]. In some embodiments, agents for enteric coatings are preferably methacrylic acid-alkyl acrylate copolymers, such as Eudragit® polymers. Poly(meth)acrylates have proven particularly suitable as coating materials. EUDRAGIT® is the trade name for copolymers derived from esters of acrylic and methacrylic acid, whose properties are determined by functional groups. The individual EUDRAGIT® grades differ in their proportion of neutral, alkaline or acid groups and thus in terms of physicochemical properties. The skillful use and combination of different EUDRAGIT® polymers offers ideal solutions for controlled drug release in various pharmaceutical and technical applications. EUDRAGIT® provides functional films for sustained-release tablet and pellet coatings. The polymers are described in international pharmacopeias such as Ph.Eur., USP/NF, DMF and JPE. EUDRAGIT® polymers can provide the following possibilities for controlled drug release: gastrointestinal tract targeting (gastroresistance, release in the colon), protective coatings (taste and odor masking, protection against moisture) and delayed drug release (sustained-release formulations). EUDRAGIT® polymers are available in a wide range of different concentrations and physical forms, including aqueous solutions, aqueous dispersion, organic solutions, and solid substances. The pharmaceutical properties of EUDRAGIT® polymers are determined by the chemical properties of their functional groups. Poly(meth)acrylates, soluble in digestive fluids (by salt formation) EUDRAGIT® L (Methacrylic acid copolymer), S (Methacrylic acid copolymer), FS and E (basic butylated methacrylate copolymer) polymers with acidic or alkaline groups enable pH-dependent release of the active ingredient. Applications: from simple taste masking via resistance solely to gastric fluid, to controlled drug release in all sections of the intestine. Poly(meth)acrylates, insoluble in digestive fluids: EUDRAGIT® RL and RS (ammonio methacrylate copolymers) polymers with alkaline and EUDRAGIT® NE polymers with neutral groups enable controlled time release of the active by pH-independent swelling. Enteric EUDRAGIT® coatings provide protection against drug release in the stomach and enable controlled release in the intestine. The dominant criterion for release is the pH-dependent dissolution of the coating, which takes place in a certain section of the intestine (pH 5 to over 7) rather than in the stomach (pH 1-5). For these applications, anionic EUDRAGIT® grades containing carboxyl groups can be mixed with each other. This makes it possible to finely adjust the dissolution pH, and thus to define the drug release site in the intestine. EUDRAGIT® L and S grades are suitable for enteric coatings. EUDRAGIT® FS 30 D (aqueous dispersion of an anionic copolymer based on methyl acrylate, methyl methacrylate and methacrylic acid) is specifically used for controlled release in the colon. In some embodiments, the probiotic *Lactobacillus* strain of the present invention is administered to the subject in the form of a food composition. In some embodiments, the food composition is selected from complete food compositions, food supplements, nutraceutical compositions, and the like. The composition of the present invention may be used as a food ingredient and/or feed ingredient. The food ingredient may be in the form of a solution or as a solid—depending on the use and/or the mode of application and/or the mode of administration.

As used herein, the term "food" refers to liquid (i.e. drink), solid or semi-solid dietetic compositions, especially total food compositions (food-replacement), which do not require additional nutrient intake or food supplement compositions. Food supplement compositions do not completely replace nutrient intake by other means. Food and food supplement compositions are for example fermented dairy products or dairy-based products, which are preferably administered or ingested orally one or more times daily. Fermented dairy products can be made directly using the bacteria according to the invention in the production process, e.g. by addition to the food base, using methods known per se. In such methods, the strain(s) of the invention may be used in addition to the micro-organism usually used, and/or may replace one or more or part of the micro-organism usually used. For example, in the preparation of fermented dairy products such as yoghurt or yoghurt-based drinks, a bacterium of the invention may be added to or used as part of a starter culture or may be suitably added during such a fermentation. Optionally the bacteria may be inactivated or killed later in the production process. Fermented dairy products include milk-based products, such as (but not limited to) deserts, yoghurt, yoghurt drinks, quark, kefir, fermented milk-based drinks, buttermilk, cheeses, dressings, low fat spreads, fresh cheese, soy-based drinks, ice cream, etc. Alternatively, food and/or food supplement compositions may be non-dairy or dairy non fermented products (e.g. strains or cell-free medium in non-fermented milk or in another food medium). In some embodiments, the probiotic *Lactobacillus* strain of the present invention is encapsulated and dispersed in a food (e.g. in milk) or non-food medium. Non-fermented dairy products may include ice cream, nutritional bars and dressings, and the like. Non-dairy products may include powdered beverages and nutritional bars, and the like. The products may be made using known methods, such as adding an effective amount of the strain(s) and/or cell-free culture medium to a food base, such as skimmed milk or milk or a milk-based composition and fermentation as known. Other food bases to which the (compositions comprising the) bacterial cells and/or cell-free culture medium may be added are meat, meat replacers or plant bases. The composition that comprises the probiotic *Lactobacillus* strain of the present invention may be solid, semi-solid or liquid. It may be in the form of a food product or food supplement, e.g. in the form of tablets, gels, powders, capsules, drinks, bars, etc. For example the composition may be in the form of a powder packed in a sachet which can be dissolved in water, fruit juice, milk or another beverage.

As used herein the term "food ingredient" or "feed ingredient" includes a formulation which is or can be added to functional foods or foodstuffs as a nutritional supplement. By "nutritional food" or "nutraceutical" or "functional" food, is meant a foodstuff which contains ingredients having beneficial effects for health or capable of improving physiological functions. By "food supplement", is meant a foodstuff having the purpose of completing normal food diet. A food supplement is a concentrated source of nutrients or other substances having a nutritional or physiological effect, when they are taken alone or as a combination in small amounts. According to the invention, "functional food" summarizes foodstuff and corresponding products lately developed to which importance is attributed not only due to them being valuable as to nutrition and taste but due to particular ingredient substances. According to the invention, the middle- or long-term maintenance and promotion of health are of importance. In this context, non-therapeutic uses are preferred. The terms "nutriceuticals", "foodsceuticals" and "designer foods", which also represent embodiments of the invention, are used as synonyms, partly, however, also in a differentiated way. The preventive aspect and the promotion of health as well as the food character of the products are, however, best made clear by the term functional food. In many cases, these relate to products accumulated by assortment and selection (as is also the case in the present invention), purification, concentration, increasingly also by addition. Isolated effective substances, in particular in form of tablets or pills, are not included. Although there is no legal definition of a functional food, most of the parties with an interest in this area agree that they are foods marketed as having specific health effects beyond basic nutritional effects. Accordingly, functional foods are ordinary foods that have components or ingredients (such as those described herein) incorporated into them that impart to the food a specific functional e.g. medical or physiological benefit other than a purely nutritional effect.

In some embodiments, the drink is a functional drink or a therapeutic drink, a thirst-quencher or an ordinary drink. By way of example, the composition of the present invention can be used as an ingredient to soft drinks, a fruit juice or a beverage comprising whey protein, health teas, cocoa drinks, milk drinks and lactic acid bacteria drinks, yoghurt and drinking yoghurt, cheese, ice cream, water ices and desserts, confectionery, biscuits cakes and cake mixes, snack foods, balanced foods and drinks, fruit fillings, care glaze, chocolate bakery filling, cheese cake flavoured filling, fruit flavoured cake filling, cake and doughnut icing, instant bakery filling creams, fillings for cookies, ready-to-use bakery filling, reduced calorie filling, adult nutritional beverage, acidified soy/juice beverage, aseptic/retorted chocolate drink, bar mixes, beverage powders, calcium fortified soy/plain and chocolate milk, calcium fortified coffee beverage.

In some embodiments, the composition that comprises the probiotic *Lactobacillus* strain of the present invention is used with yoghurt production, such as fermented yoghurt drink, yoghurt, drinking yoghurt, cheese, fermented cream, milk based desserts and others. Suitably, the composition can be further used as an ingredient in one or more of cheese applications, meat applications, or applications comprising protective cultures.

The food composition that comprises the probiotic *Lactobacillus* strain of the present invention typically comprises carriers or vehicles. "Carriers" or "vehicles" mean materials suitable for administration and include any such material known in the art such as, for example, any liquid, gel, solvent, liquid diluent, solubilizer, or the like, which is non-toxic and which does not interact with any components of the composition in a deleterious manner. Examples of nutritionally acceptable carriers include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

In some embodiments, the food composition that comprises the probiotic *Lactobacillus* strain of the present invention comprises an amount of dietary fibres. Dietary fibre passes through the small intestine undigested by enzymes and functions as a natural bulking agent and laxative. Dietary fibre may be soluble or insoluble and in general a blend of the two types is preferred. Suitable sources of dietary fibre include soy, pea, oat, pectin, guar gum, gum Arabic, fructooligosaccharides, galacto-oligosaccharides, sialyl-lactose and oligosaccharides derived from animal milks. In some embodiments, the dietary fiber is selected among mannans. Mannans (such as glucomannans and galactomannans), such as guar gum, locust bean gum, konjac, and xanthan gum, are present in some plant cell walls. The glucomannans are generally comprised of (1-4)-β-linked glucose and mannose units, while the galactomannans are generally comprised of a (1-4)-β-mannan backbone substituted with single units of (1-6)-α-galactose. Many endospermic legumes, such as guar and locust bean, contain galactomannans in the endosperm during seed development. Glucomannans have also been found as a minor component of cereal grains.

In some embodiments, the composition that comprises the probiotic *Lactobacillus* strain of the present invention contains emulsifiers. Examples of food grade emulsifiers typically include diacetyl tartaric acid esters of mono- and di-glycerides, lecithin and mono- and di-glycerides. Similarly suitable salts and stabilisers may be included.

In some embodiments, the food composition that comprises the probiotic *Lactobacillus* strain of the present invention contains at least one prebiotic. "Prebiotic" means food substances intended to promote the growth of the probiotic *Lactobacillus* strain of the present invention in the intestines. The prebiotic may be selected from the group consisting of oligosaccharides and optionally contains fructose, galactose, mannose, soy and/or inulin; and/or dietary fibers.

In some embodiments, the composition that comprises the probiotic *Lactobacillus* strain of the present invention contains protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents, gel forming agents, antioxidants and antimicrobials. The composition may also contain conventional pharmaceutical additives and adjuvants, excipients and diluents, including, but not limited to, water, gelatine of any origin, vegetable gums, ligninsulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like. In all cases, such further components will be selected having regard to their suitability for the intended recipient.

In some embodiments, the administration of the probiotic *Lactobacillus* strain is repeated, for example, 2 to 3 times a day, for one day or more and generally for a sustained period of at least 4 days, or even 4 to 15 weeks, with, where appropriate, one or more periods of interruption. In some embodiments, the probiotic *Lactobacillus* strain is administered simultaneously or sequentially one meal of the subject.

As used herein, the term "effective amount" refers to a quantity sufficient of the probiotic *Lactobacillus* strain to achieve the beneficial effect (e.g. restoring the incretin effect of GLP-1). In the context of the present invention, the amount of the probiotic *Lactobacillus* strain administered to the subject will depend on the characteristics of the individual, such as general health, age, sex, body weight . . . . The skilled artisan will be able to determine appropriate dosages depending on these and other factors. For example, the probiotic *Lactobacillus* strain shall be able to generate a colony is sufficient to generate a beneficial effect on the subject. If the probiotic *Lactobacillus* strain is administered in the form of a food product, it typically may comprise between $10^3$ and $10^{12}$ cfu of the probiotic *Lactobacillus* strain of the present invention per g of the dry weight of the food composition.

Typically, the incretin-based drug is administered to the subject in the form of a pharmaceutical composition. Typically, the incretin-based drug may be combined with pharmaceutically acceptable excipients, and optionally sustained-release matrices, such as biodegradable polymers, to form therapeutic compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The Incretin-based drug and the probiotic Lactobacillus strain can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the typical methods of preparation are vacuum-drying and freeze-drying techniques which yield a powder of the active ingredient plus any additional desired ingredient from a previously sterile-filtered solution thereof. The preparation of more, or highly concentrated solutions for direct injection is also contemplated, where the use of DMSO as solvent is envisioned to result in extremely rapid penetration, delivering high concentrations of the active agents to a small tumor area. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject. A further object of the present invention relates to a pharmaceutical composition comprising at least one probiotic Lactobacillus strain and at least one incretin-based drug.

A further object of the present invention relates to a method for predicting the response of a patient to a GLP-1 receptor agonist, said method comprising:
 i) Determining the Lactobacillus genus frequency in the gut of said patient;
 ii) Comparing the value obtained at step i) with a predetermined reference value;
 iii) Concluding that the patient will develop a resistance to a GLP-1 receptor agonist when the value determined at step i) is lower than the predetermined reference value or concluding that the patient will not develop a resistance to a GLP-1 receptor agonist when the value determined at step i) is higher than the predetermined reference value.

For example, the Lactobacillus genus frequency is determined from a patient feces sample in which the frequency is determined using any polymerase chain reaction techniques.

As used herein, the term "predicting" refers to a probability or likelihood for a subject to develop an event. Preferably, the event is herein resistance to a GLP-1 receptor agonist.

As used herein, a predetermined reference can be relative to a number or value derived from population studies, obtained from the general population or from a selected population of subjects. Such predetermined reference values can be derived from statistical analyses and/or risk assessment data of populations obtained from mathematical algorithms and computed indices. The predetermined reference value can be a threshold value or a range.

The term "developing a restistance to GLP-1 receptor agonist" means that the administration of GLP-1 receptor agonist to said subject does not produce the desired therapeutic effects or partially.

The invention will be further illustrated by the following figures and examples. However, these examples and figures should not be interpreted in any way as limiting the scope of the present invention.

FIGURES

Figure 1B:
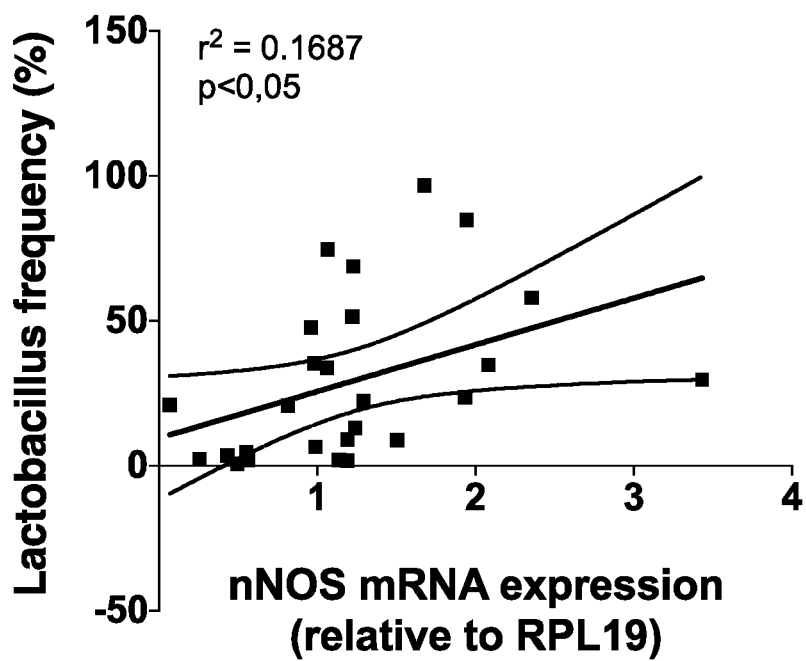

FIG. 1: Gut microbiota dysbiosis is responsible for the GLP-1 resistance. A-C: Mice were fed 3 months with NCD, HC-HFD or HFD. (A) nNOS or (B) GLP-1r ileum mRNA concentrations and Lactobacillus genus frequency; (C) Lactobacillus genus frequency. Values with similar superscript letter are not different, $p > 0.05$. The values are compared between NCD and HC-HFD and HFD-fed mice.

FIG. 2: Combination treatment with Lactobacilli and a GLP-1 receptor agonist for the treatment of glycaemia of type 2 diabetic mice. A) Glycaemic index B) Insulin.

EXAMPLE 1

Methods:
Animals.
C57BL/6 wild type (WT), TLR4, CD14 and NOD2 knockout (KO) male mice were initially purchased from the Charles Rivers laboratories. The GLP-1 receptor knockout (GLP-1rKO) male mice were a kind gift from DJ Drucker's laboratory (Toronto, Canada). Mice were housed in a controlled environment (inverted 12 h daylight cycle, light off at 10:00 a.m.) with free access to food and water. To generate metabolic abnormalities of type 2 diabetes, six-week old mice were fed for three months with a normal chow diet (NCD: proteins 22%, carbohydrates from cereal origins: starch and fiber; 67%, lipids 11% of total kcal, Safe), or a high-fat high-carbohydrate diet (HC-HFD: proteins 20%, carbohydrates as sucrose, maltodextrin, and fiber; 20%, lipids 60% of total kcal, Research Diet), or a high-fat carbohydrate-free diet (HFD: proteins 22%, carbohydrates <1%, 78% lipids of total kcal, Safe). The impact of gut microbiota was analyzed following a 3 months diet treatment. After 2 months of diet, a sub group from these mice was treated for one additional month with antibiotics (Ampicillin, Neomycin, Metronidazol 0.1 g/100 ml of each in water, in free access). Eight-week old C57BL/6 germ-free male mice (TAAM, Orléans, France) were colonized by gavage with the mucosal microbiota from the ileum of mice fed for 3 months with a HFD or a HC-HFD. The ileum microbiota from 3 mice of each group was pooled and suspended in sterile reduced PBS (gaz N2 and thioglycolic acid, sigma Aldrich, St Louis France). The germ-free mice were gavaged with 200 µl of the ileum suspension and kept in sterile isolator for 2 weeks. All animal experimental procedures were approved by the local ethical committee of the Rangueil hospital and by the local ethical committee of the University of Paris Diderot.

Subdiaphragmatic Vagotomy

To study the role of GLP-1 on the gut to brain axis, mice underwent a subdiaphragmatic vagotomy (Hosoi, 2002). They were anesthetized by intraperitoneal injection of Ketamin (100 mg/kg) and Xylasin (10 mg/kg) and maintained under isofluran (0.5 to 1% of air). From an upper midline laparotomy (2 cm), vagal trunks were exposed and 1 cm of the visible ventral vagus nerve and all neural and connective tissues surrounding the esophagus were cut off. For sham-operated animals, the vagus nerve was similarly exposed but not cut. The efficacy of the vagotomy was assessed two weeks later by measuring the satiety effect of cholecystokinin-octapeptide (CCK-8), in 16 hours-fasted operated mice following an injection with saline or CCK-8 (8 µg/kg, intraperitoneally). 5 min after injection, the amount of food ingested was measured for 30 min. The mice that did not respond to the stimulus were discarded. All experiments were realized one week after CCK-8 test.

Glucose and Insulin Tolerance Tests, Plasma and Tissue Sample Collection.

After 3 months of HFD, an intraperitoneal (i.p.) glucose tolerance test (IPGTT) and an i.p. insulin tolerance test (IPITT) were performed. Mice fasted for 6 h or 4 h were injected with glucose for IPGTT (1 g/kg) or insulin for IPITT (0.75 U/kg), respectively, into the peritoneal cavity. One microliter from the tip of tail blood was collected before and for up to 90 min. following the glucose or insulin challenges to quantify the concentration of glucose using a glucose-meter (Accu Chek, France).

To identify oral glucose-induced insulin and GLP-1 secretions, all sets of mice were gavaged with glucose (2 g/kg). After 15 min, 30 µl of blood from the tip of the tail vein were sampled to assess plasma insulin concentration. 300 µl of portal vein blood were collected following an intravenous (i.v.) administration of a Ketamin (10 mg/kg)/Xylasin (1 mg/kg), to ensure an immediate anesthesia of the mice. This procedure allows performing portal vein blood sampling since it dramatically minimizes the impact of anesthesia on blood parameters. In addition, to prevent from the in vivo degradation of GLP-1 by DPP4, a DPP4 inhibitor (400 µg/mouse sitagliptin, MSD Rahway, N.J.) was administered orally 30 min before the oral gavage with glucose. Eventually, the portal blood was collected in the presence of protease inhibitors diprotin A (1 mM), aprotinin (0.2 µM) and EDTA (1 mM). Plasma hormones were assessed by ELISA (insulin, Mercodia; active GLP-$1_{7-36}$, Alpco). A GLP-1 resistance index for each mice was calculated from glucose, insulin and GLP-1 concentrations 15 min after the oral glucose load. Since the insulinotropic activity of GLP-1 depends upon the glycemic level we set the following equation: Glucose x GLP-1 concentrations/insulin concentration. In some experiments, distal ileum and left nodose ganglion were harvested from mice.

In Vivo GLP-1 Dose-Response Procedures.

To evaluate GLP-1 sensitivity three GLP-1 regulated parameters were quantified: insulin secretion, gastric emptying, and food intake. To prevent from the degradation of exogenous GLP-1 a DPP4 inhibitor (400 µg/mouse sitagliptin) was given orally 30 min before the GLP-1 challenge.

Since GLP-1 insulinotropic effect is glucose dependent we first assessed in vivo GLP-1 stimulated insulin secretion in hyperglycemic conditions. The mice were first fasted for 6 h before the GLP-1 and glucose challenges. Active GLP-$1_{7-36}$ (BACHEM, Switzerland) was then administered intraperitoneally at different doses (0, 2.2, 7, 20, 63 nmol/kg, diluted in distilled water) 5 min before the glucose challenge. In some sets of experiments a single active dose of 7 nmol/kg was tested. To induce hyperglycemic conditions a retrorbital i.v. glucose (1 g/kg) injection was realised. This procedure avoids the confounding effect of the oral glucose-induced gut-secreted GLP-1. Blood (30 µl) was collected from the tail vein 15 min after glucose challenge. Plasma insulin concentration was determined.

For gastric emptying the glucose challenge was replaced by an oral administration of acetaminophen (SIGMA-Aldrich, 100 µg/kg). The plasma acetaminophen concentrations were assessed by colorimetric-based assay (SEKISUI diagnostics, Canada) in the plasma from tail blood during 15 min.

Food intake was recorded for 30 min following a 16-hour period of fast.

The dose-response curve was calculated by curve interpolation with 4-Parameter Logistic (4PL) sigmoidal model using GraphPad Prism version 6.00 for Mac (GraphPad Software, San Diego, Calif., USA; www.graphpad.com) and the ECso calculated.

In Vivo Nitric Oxide Related Procedures.

Thirty minutes before all 3 GLP-1 challenge procedures, a NO synthase (NOS) inhibitor (L-NAME, Abcam) was administered i.p. at doses of 0, 50, 100, 200 µg/kg. In a different set of mice, a NO donor (L-Arginine, 1 g/kg, Sigma-Aldrich) was administered orally in the presence or absence of the GLP-1r antagonist, Exendin 9 (1 nmol/mice, 100 µL, i.p. injection, Bachem). To study the chronic effect of L-arginine in GLP-1 sensitivity, the molecule (0.5 g/kg, 300 µL, lgavage/day) was administered for one week. Then, GLP-1-induced insulin secretion was quantified.

mRNA Quantification

Total RNAs were extracted with TriPure Reagent from the ileum and with RNAeasy Microkit, (Qiagen) from the nodose ganglion. The concentration of mRNAs was evaluated by quantitative RT-PCR analysis. PCRs were performed using ViiA7 (Applied Biosystems, Foster City, Calif., USA). The concentration of each mRNA was normalized for RNA loading for each sample using RPL19 rRNA as an internal standard.

Immunohistochemistry

Longitudinal Muscle/Myenteric Plexus

To prepare longitudinal muscle/myenteric plexus (LMMP, i.e. enteric nervous system) 3 cm of distal ileum obtained from mice in a fed state, were cut longitudinally and soaked in a Silgard coated plate containing ice-cold PBS. The mucosal layer was removed and the LMMP was dropped into paraformaldehyde (PFA) 4% overnight, at room temperature (RT) washed with cold PBS and kept in a sodium azide solution (0.1% in PBS) at 4° C. Samples were blocked for 1 h at room temperature (RT) with PBS containing Triton X100 (0.5%), sodium azide (0.1%) and goat serum (4%). For HuC/HuD immunostaining, bovine serum albumin (BSA, 4%) was added to the previous solution. Then samples were incubated overnight at RT with the primary antibodies diluted in the blocking solution (HuC/HuD, Lifetechnologies; S100b, Abcam; or nNOS, R&D system; 1/500), washed 3 times with PBS, incubated 90 min at RT with the secondary antibodies (Alexa 488 or Alexa 568, Lifetechnologies; 1/400) and washed 3 times with PBS. Samples were mounted with fluorescent mounting medium (Dako). The fluorescence of different tissues was measured on confocal Zeiss Laser Scanning Microscope LSM-780 equipped with 20×/0.8 NA objective and Black Zen software and analysed with Image J software. For HuC/HuD and nNOS, we quantified the number of positive cells per area and for S100b, we quantified the percentage of fluorescent area.

c-FOS Immunostaining in the Brain Stem 90 min following the GLP-1-induced insulin secretion challenge procedure mice were anesthetized with pentobarbital and tissues were fixed by intra-cardiac injection of PFA 4% diluted in PBS. Brain was removed and kept on PFA 4% overnight at 4° C. After washing in cold citrate buffer for 6 h, brain was warmed until boiling, washed in PBS, cooled to 4° C., then immersed in cold sucrose solutions (10% then 30% in PBS). After freezing on dry ice, the brain was stored at −80° C. and cut into 20 µm thick slices (cryostat, Thermo). The slices were washed 3 times with PBS, blocked with PBS, 0.3% Triton X100, 2% donkey serum and incubated with the c-fos antibody diluted in the same solution (1/10000, Santa Cruz) overnight at RT. After 16 h, the brain slices were washed 3 times with PBS and incubated with biotinylated antibody (1/2000, Jackson ImmunoResearch) diluted in the PBST solution (PBS, 0.3% Triton X100) for 1 h at RT. Brain slices were washed 3 times in PBS and incubated with the reagent A (avidin) and B (biotinylated enzyme) from Vectastain Elite ABC kit (Vector Laboratories) diluted in the PBST solution, 30 min at RT. Then, brain slices were washed 3 times in PBS and incubated with biotinylated tyramine solution (tyramine and biotin diluted in borate buffer/3% $H_2O_2$, pH=8.4), 20 min at RT. After 3 washes in PBS, samples were incubated with alexa 568 conjugated streptavidin diluted in the blocking solution (1/1000, Lifetechnologies), during 3 h, at 37° C. Brain slices were washed five times with PBS. Samples were mounted with fluorescent mounting medium (Dako). The fluorescence was analysed as above. We identified the Nucleus Tractus Solitary NTS and dorsal motor nucleus of vagus nerve DMNX area using a mouse brain atlas (Franklin and Paxinos, 1997) and we counted the number of cFOS positive cells/area corresponding to the NTS-DMNX.

Ex Vivo Ileal Real-Time NO Measurement

The distal ileum segment from fed mice were washed in Krebs-Ringer bicarbonate/glucose buffer (pH 7.4) in an atmosphere containing 95% O2—5% CO2 and then immersed in Eppendorf tubes containing 400 µL of the same medium. After a 10 min recovery period, the spontaneous NO release in response to 10 µL of Krebs-Ringer solution (control), GLP-1 (150 nM) and/or Exendin 9 (375 nM) was measured at 37° C. for 10 min using a NO-specific amperometric probe (ISO-NOPF, 100 nm diameter, 5 mm length, World Precision Instruments, Aston Stevenage, UK) implanted directly in the ileum. Data are expressed (Fournel et al., 2015).

Enteric Neurons Primary Culture

The protocol was adapted from Smith and colleagues (Smith et al., 2013). The ileum (last 9 cm) was harvested and kept in ice cold-carbogen bubbled-Krebs solution. The tissue was cut into 3 cm slices and kept on plastic rod. An incision was realized with a forceps where the mesentery was attached. The outer layers containing muscular cells and myenteric neurons (LMMP) were obtained by moving from top to bottom, along the gap. The LMMP were digested with collagenase II (1.3 mg/mL, Worthington) and BSA (0.3 mg/mL) in Krebs solution bubbled with carbogen 30 min in a 37° C. shaking bath. Digested cells were transferred in Hank Balanced salt Solution (HBSS)/trypsin solution (0.05%) 7 min in a 37° C. shaking bath. Trypsin was neutralized with the rince media (F12 media from SigmaAldrich with 10% FBS and antibiotic/antimycotic 1x from Gibco) and the digested cells were filtered on nitex mesh (500 µm) and transferred to complete neuron media (Neurobasal A media with B-27 supplement 1× from Life Technologies, 2 mM L-glutamine, 1% FBS, 0.1% glial-derived neurotrophic factor from Neuromics and antibiotic/antimycotic 1×). Primary cells were maintained up to one week in Poly-D-lysine (Sigma-Aldrich) and Laminin (BD Bioscience) coated-glass coverslips in 24-wells plate in an incubator (37° C., 5% $CO_2$) and the complete neuron media was changed every 2 days.

Measurement of NOS Activity in Primary Cultures of Neurons

Primary enteric neurons were grown for 7 days in culture. To record NO production the neurons were washed 2 times with HEPES buffer pH 7.38 and incubated with the NO specific probe, DAF-FM (2 µM, Molecular Probes) for 30 min. Cells were washed twice with HEPES Buffer and kept 15 min in the incubator. Then, cells were stimulated with active GLP-1$_{7-36}$ diluted in HEPES buffer, at different concentrations (0.0001, 0.001, 0.01, 0.1, 1, 10 and 100 nM, BACHEM) during 15 min and kept in the incubator. After GLP-1 stimulation, cells were washed twice with PBS buffer, fixed with PFA 4%, washed twice with PBS and once with PBS/Triton X100 (0.1%) and saturated with BSA 1% 30 min at RT. Positive cells for nNOS were identified following nNOS immunostaining with nNOS antibody (1/300, BSA 1%, Abcam) overnight at 4° C. Cells were washed twice with PBS, once with PBS/Triton X100 (0.1%) and incubated with an Alexa 568 antibody (1/800, BSA 1%, Lifetechnology) 1 h at RT. After 3 washes with PBS and incubation with DAPI 5 min at RT, cells were washed 3 times with PBS and mounted with fluorescent mounting medium (Dako). The fluorescence was measured on confocal Zeiss Laser Scanning Microscope LSM-780 equipped with 63×/1.4 NA oil immersion objective and a GaAsP detector with quantum yield of 45% with Black Zen software and analysed with Image J software. A region of interest (ROI) corresponding to identified nNOS positive cells was defined from where the DAF-FM or nNOS fluorescence mean per ROI was measured. The ratio of both values for each ROI was then calculated.

Statistical Analysis

Results are expressed as mean±standard error of the mean (SEM). Satistical significance was evaluated by Student's t test, One-Way Anova or Two-Way Anova (followed by post hoc Tukey's multiple comparisons tests), using GraphPad Prism version 6.00 for Mac (GraphPad Software, San Diego, Calif., USA; www.graphpad.com). Linear regression was performed with Pearson correlation coefficient. The level of significance was set at $P<0.05$.

Results:

Animal Models of High-Fat Diet-Induced GLP-1 Resistance.

To identify whether gut microbiota regulates GLP-1 action in vivo, we have set up two different mouse models previously characterized with a gut microbiota dysbiosis (Everard et al., 2014; Garidou et al., 2015; Serino et al., 2012). A first set of mice was fed a high-carbohydrate high-fat diet (HC-HFD). The second one was fed a high-fat but carbohydrate-free diet (HFD). We and others have previously characterized the main metabolic features of both animal models (Burcelin et al., 2002; Everard et al., 2013). Briefly, mice fed a HC-HFD are obese and diabetic whereas mice fed a HFD are diabetic by remained mainly lean. Both models are characterized by a similar glucose intolerance and an impaired insulin resistance. However, the major difference between both models is that 15 minutes after an oral glucose challenge, plasma insulin concentration was twice higher in HC-HFD obese diabetic mice or reduced in HFD-fed mice when compared with NCD-fed lean diabetic mice. The mechanisms are unknown but could be related to impact of the high proportion of lipids in the diet associated to the absence of carbohydrate in the lean diabetic group. A reduced whole body glucose sensitivity caused by lipotoxicity could be thought as well (Moore et al., 2004; Poitout and Robertson, 2008). A mechanism responsible for the impaired glucose sensitivity could be related to a reduced glucose-induced GLP-1 secretion. Therefore, we quantified GLP-1 secretion in response to oral glucose and observed that the impaired glucose-induced insulin secretion of the lean diabetic group was not associated with a reduced portal vein plasma GLP-1 concentration but conversely with a major increase of portal vein plasma GLP-1 concentration 3-4 times higher that what observed when compared to NCD-fed mice. The increased plasma GLP-1 concentration was to be compared with that of the HC-HFD mice since they were also characterized by an increased glucose-induced GLP-1 secretion. Therefore, the excessive plasma GLP-1 concentrations observed in both animal models of diabetes seemed linked to the fat-enriched diet and the diabetic state rather than to the lean or obesity phenotypes. This was previously observed in response to high-fat diet (Yang et al., 2016) and we here confirmed this result. However, the major novel observation was that despite the excessive plasma GLP-1 secretion of both animal models, glucose-induced insulin secretion could be triggered only in HC-HFD obese diabetic mice since plasma insulin secretion remained low in the HFD-fed lean diabetic mice. In our experimental conditions, where a DPP4i was administered to the mice just before the glucose challenge, the portal concentration of GLP-1 reflects the actual secretion of GLP-1, as described (Waget et al., 2011), preventing from putative differences of DPP4 activities between groups which could have modified the concentration of GLP-1. Since at the 15 minutes time point following the glucose challenge, NCD and HC-HFD-fed mice were characterized by the same glycemia while HFD-fed mice glycemia was lower. We then calculated a glucose-dependent GLP-1-induced insulin secretion index and showed that the HFD-fed lean diabetic mice were characterized by a strong GLP-1 resistance, which was not the case for the HC-HFD-fed obese diabetic mice. To better estimate GLP-1-induced insulin secretion without the confounding effect of endogenously released GLP-1, we administered GLP-1 intraperitoneally at different doses followed an i.v. glucose injection. Plasma glucose concentrations increased in all groups generating a hyperglycemic context. Plasma insulin concentrations were then quantified at the 15 minute time point following the glucose challenge. The injection of 7 nmol/kg of GLP-1 allows reaching the maximal insulin secretion in NCD and HC-HFD-fed mice. However, this was not the case for the HFD-fed lean diabetic mice suggesting that GLP-1 sensitivity was impaired. The dose-response curve corresponding to the fold change of GLP-1-induced insulin secretion allows the calculation of EC50. The data show that the EC50 was doubled in HC-HFD mice and dramatically increased in the HFD-fed lean diabetic mouse group when compared to NCD mice demonstrating a state of resistance to GLP-1 in both models (FIG. 3I). Altogether, our data show that only lean-diabetic mice are strongly GLP-1 resistant. This observation corroborates what observed in subsets of T2D patients since in large clinical trials the efficacy of DPP4i or GLP-1 agonist therapies varies according to the patient as shown by the standard deviation. Furthermore, overtime the efficacy of the incretin-based drug vanishes in some patients and not in others that also suggests a change in GLP-1 action during the evolution of the disease (Toyoda et al., 2014). In humans, the change in efficacy of incretin-based drug is mostly evaluated on the change in HbA1c. This biomarker integrates the overall glycemic profiles over a 2-3 month period that are the consequences of changes in insulin and glucagon secretions, reduced gastric emptying, increased food intake and insulin resistance. Therefore, to determine whether GLP-1 resistance affected other GLP-1 regulated physiological functions, we studied gastric emptying and food intake. Although basal gastric emptying was similar in all groups, some degree of GLP-1 resistance was detected since the plasma concentrations of acetaminophen remained elevated after GLP-1 administration in both fat-enriched diet-fed mice. Like insulin secretion, gastric emptying is a mediated physiologically through the activation of a nervous gut-stomach axis. In fact, GLP-1 secreted after a meal induces the ileum break through a reduction of gastric, pyloric and duodenal motility (Imeryuz et al., 1997; Tolessa et al., 1998). Therefore, our data show that GLP-1 resistance is upstream in the cascade of events responsible for GLP-1 action and most likely concerns the gut-brain to periphery axis. Data from our laboratory demonstrated in type 1 diabetic patients that the glucagonostatic action of DPP4i was dramatically hampered in those with autonomic neuropathy preventing from the activation by gut released GLP-1 of the gut-brain to alpha cell axis (Lobinet et al., 2015). This conclusion is also supported by the present data since GLP-1 resistance was similarly detected regarding feeding behavior for the HFD-fed lean diabetic mice. The amount of energy intake during the feeding period (darkness) and during refeeding following a fasting period was increased. Furthermore, increasing doses of GLP-1 only modestly reduced energy intake when compared to NCD-fed mice. The control of food intake by GLP-1 is mediated by the central nervous system and the peripheral nervous system (Krieger et al., 2015) showing that all nervous system-dependent actions are affected by GLP-1 resistance.

Altogether, a fat-enriched diet favors a general state of GLP-1 resistance that seems to affect nerve dependent GLP-1 actions. Importantly, out of the two fat-diet models, the HFD-fed lean diabetic mouse model was the most affected one and was defined as GLP-1 resistant. Conversely, only very mild GLP-1 resistance was detected in the carbohydrate containing high-fat diet-fed obese diabetic mouse. We defined this mouse model as more GLP-1 sensitive. The molecular mechanisms of this difference in GLP-1 sensitivity are yet unknown. They could affect directly the insulin-secreting beta cell and indirectly the GLP-1 sensitive neural mechanism notably the gut-brain axis that involves the action of GLP-1 on neurons from the enteric nervous system and the vagus nerve (Amato et al., 2010; Fujiwara et al., 2012; Imeryuz et al., 1997; Nishizawa et al., 2013; Tolessa et al., 1998; Waget et al., 2011; Wichmann et al., 2013). To discriminate between both hypotheses, we studied insights of neuropathy in the mouse and performed vagotomy in NCD-fed mice.

High-Fat Diet Alters the Enteric Nervous System to Brain Axis and Induces GLP-1 Resistance.

GLP-1 triggers the vagus nerve activity in response to an oral glucose challenge (Imeryuz et al., 1997; Nishizawa et al., 2013; Waget et al., 2011) that could be linked to the presence of the GLP-1 receptor at the plasma membrane of enteric and vagal neurons (Richards et al., 2014). Therefore, we first quantified by immunohistochemistry the number of HuC/HuD positive cells, i.e. enteric neurons (Stenkamp-Strahm et al., 2013). The results show that the GLP-1 resistant HFD-fed mice were characterized by a reduced number of enteric neurons that defines neuropathy, as described (Stenkamp-Strahm et al., 2013). Conversely, the number of S100β positive cells, i.e. glial cells (Kabouridis et al., 2015), remained normal, or even slightly increased in the HC-HFD-fed mice showing that only the number of neurons was affected by the fat-diet. To comfort the reduction of the number of enteric neurons in the HFD-fed lean diabetic mouse group, we quantified the concentrations of ileum mRNA encoding for neuronal proteins, i.e. PGP9.5, axonal protein, i.e. peripherin (prph) and glial proteins i.e. GFAP and S100β. PGP9.5 mRNA concentration was reduced in both animal models of fat-enriched diets while prph, GFAP and S100β mRNA concentration remained unchanged. Importantly, the impact of the diet was restricted to neurons from the enteric nervous system as the concentration of the mRNA encoding neuronal and glial proteins from the nodose ganglion remained similar in all groups demonstrating some degree of specificity of the impairment. These results reflect that diabetic autonomic neuropathy does not affect vagal neurons but first of all, axons (Landowski et al., 2016) while it affects strongly enteric neurons (Stenkamp-Strahm et al., 2013). These results suggest that the enteric neurons rather than the vagus nerve neurons were affected by the fat-diet. These first features further suggest that the gut-brain axis could be impaired by the fat-enriched diets, which is although not linked to the fat component itself since the quality was similar in both groups. This is in line with the concept that GLP-1 resistance also affects subsets of type 2 diabetic patients at different extent. To demonstrate that, the gut-brain axis was functionally affected, we then performed a functional bioassay to trace the action of GLP-1 on the gut-brain axis. We recorded the number of cFos positive cells in the brain stem in response to the administration of GLP-1 at the active dose i.e. 7 nmol/kg in the dorsal vagal complex of the hindbrain medulla. This dose is the lowest one triggering the maximal response to GLP-1-induced insulin secretion. The hindbrain medulla includes the nucleus of the solitary tract where primary visceral afferents end. It also includes the dorsal motor nucleus (DMNx) where preganglionic motor neurons innervating the gastrointestinal tract are located. The data show that the number of cFos positive neurons increases in response to GLP-1 in NCD mice but not in both models of high-fat diet fed mice arguing for a functional impairment of the GLP-1 dependent gut-brain communication in response to a fat diet. The activation of brain stem neurons through enteric rather than systemic GLP-1 has been previously described (Baumgartner et al., 2010; Ruttimann et al., 2009). GLP-1, when directly infused in hepatoportal vein of rats, was highlighting cells from the NTS through vagal nerve witnessing the direct GLP-1 dependent gut-brain connection, as reported also elsewhere (Baumgartner et al., 2010; Ruttimann et al., 2009). The role of the molecular glucose sensing regulators such as the GLP-1 receptor and the glucose transporter GLUT2 were also reported as molecular regulators of the glucose-dependent gut-brain axis for the glycemic control, as studied in NCD condition (Burcelin et al., 2001; Burcelin et al., 2000). Therefore, we here add to the knowledge that a fat-enriched diet hampers the gut-brain axis. We further validated this observation by assessing GLP-1 sensitivity in NCD-fed mice where the subdiaphragmatic vagal ramification was cut (SDVx). The vagotomy strongly increased GLP-1 resistance. Furthermore, the sensitivity to GLP-1 for the control of insulin secretion was assessed following injections of GLP-1. The GLP-1-induced insulin secretion at the active dose of 7 nmol/kg was reduced by the vagotomy procedure further demonstrating the importance of a functional gut-brain axis as the mode of action of GLP-1. We also evaluated whether vagotomy affected other features of GLP-1 action such as gastric emptying and food intake. The data show that vagotomy doesn't affect the basal gastric emptying but induces GLP-1 resistance to gastric emptying. Interestingly, energy intake during the feeding period, in response to refeeding and after GLP-1 administration was similar between sham and SDVx-operated mice. This data suggests that the regulatory role of GLP-1 when administered pharmacologically is, at least in part, direct on the brain and does not uniquely require the gut-brain axis for the control of food intake only.

Altogether, the impairment of GLP-1 physiological actions such as insulin secretion and gastric emptying induced by vagotomy mimicked what observed in response to HFD i.e. the GLP-1 resistant diabetic lean mouse model. This conclusion further reinforces the role played by an impaired enteric nervous system on the induction of GLP-1 resistance through the gut-brain axis. Our results are supported by data from humans following trunk vagotomy where it was reported an increased glucose-induced GLP-1 secretion, an increased gastric emptying but a reduced incretin-induced insulin secretion suggesting a state of GLP-1 resistance (Plamboeck et al., 2013) as we reported here in HFD-fed and SDVx-operated mice. Although GLP-1 triggers the vagus nerve (Fujiwara et al., 2012; Imeryuz et al., 1997; Nishizawa et al., 2013; Waget et al., 2011), some data show that the gut-brain axis is not required for GLP-1-based therapies to induce insulin secretion (Veedfald et al., 2016). This is most likely due to the large doses used, which are extremely high allowing a direct action of exogenous GLP-1 on pancreatic beta cells. It is noticeable that, in our study we cannot definitely rule out a state of beta-cells GLP-1 receptor unresponsiveness exists.

To validate our hypothesis in human, specific clinical trials must be set up where non obese T2D patients would be compared to obese diabetics. In fact, the proportion of lean diabetic patients tends to increase, particularly in developing countries (George et al., 2015). Similarly, the impact of autonomic diabetic neuropathy on the efficacy of GLP-1 based therapies in T2D patient remains to be studied. Such results could help the clinician to determine the best therapeutic strategy performing hence evidence-based precision medicine.

Enteric GLP-1 Sensitivity Requires the Production of NO by Enteric Neurons that is Impaired in HFD-Fed Mice.

To identify the enteric neuron molecular mechanisms responsible for GLP-1 resistance, we first quantified the concentration of GLP-1r mRNA in the ileum of the different mouse models. It is noteworthy that recent data show that the expression of the GLP-1 receptor gene is restricted in enteric neurons within the ileum and in the left nodose ganglion (Richards et al., 2014) that projects vagus nerve afferences in the gut. We observed that in HFD-fed mice the concentration of the GLP-1 receptor mRNA was dramatically reduced in both the ileum and left nodose ganglion whereas in HC-HFD obese diabetic mice the decrease of the GLP-1 receptor mRNA concentration was restricted to the nodose ganglion. These results could explain GLP-1 resistance as it mimics what observed in GLP-1 receptor KO mice regarding insulin secretion, gastric emptying and food intake. The impaired GLP-1 signaling in the enteric neurons could be linked to nNOS since the GLP-1 receptor mRNA concentration is mainly located in nNOS positive enteric neurons (Amato et al., 2010; Richards et al., 2014). We and others have previously demonstrated that a NO-dependent GLP-1 signaling in the brain controls blood flow and gastric emptying (Cabou et al., 2011; Ding and Zhang, 2012; Rotondo et al., 2011). Both actions control glucose metabolism. Similarly, GLP-1 is able to act on the enteric nervous system by decreasing the excitatory cholinergic neurotransmission through presynaptic GLP-1r, which modulate NO release (Amato et al., 2010). GLP-1 receptor agonist molecules such exendin-4 and liraglutide can significantly increase phospho-Akt and phospho-eNOS concentrations indicating activation of the p-Akt/p-eNOS signaling pathways (Ishii et al., 2014). Eventually, data show that in endothelial cells GLP-1 induces eNOS-mediated NO production through the triggering of the AMP-activated Kinase pathway (Li et al., 2016). Supported by these data, we here investigated the role of GLP-1-induced NO production by enteric neurons as a molecular mechanism responsible for the activation of the gut-brain axis in response to GLP-1 and the control of insulin secretion, gastric emptying, and food intake. We first measured the nNOS mRNA concentrations in the ileum and in the left nodose ganglion in all animal models and observed a decreased concentration in the ileum that was even more marked in the left nodose ganglion of the HFD-fed, GLP-1-resistant mice. In HC-HFD mice, we observe a decrease of nNOS mRNA concentration in left nodose ganglion only. Interestingly, the number of nNOS positive neurons in the ileum is not changed between all groups of mice. Linear regression analyses between nNOS and GLP-1 receptor mRNA concentrations show a strong correlation when quantified in both the ileum and the nodose ganglion suggesting a causal relationship. Altogether, the mRNA concentration analyses suggested that HFD-induced GLP-1 resistance could be linked to an impaired GLP-1 receptor expression and the corresponding induction of NO production through nNOS signaling. To further demonstrate this hypothesis we treated mice with different doses of the nNOS inhibitor (L-NAME). This procedure partially reduced GLP-1-induced insulin secretion in NCD mice. Similarly, we evaluate the effect of L-NAME in others GLP-1 actions. The NOS inhibitor altered GLP-1-induced gastric emptying inhibition but not GLP-1-induced food intake inhibition. Conversely, the oral and acute treatment with the NO donor L-Arginine, before an oral glucose challenge in NCD-fed mice, induced insulin secretion. This increased insulin secretion was specific to the action of GLP-1 since the co-treatment with Exendin 9 prevented the effect of GLP-1. In the same way, L-Arginine can induce gastric emptying inhibition through the GLP-1r but not the food intake reduction. Therefore, we next evaluated the impact of the NO-donor in HFD-GLP-1 resistant mice. An oral and acute administration of the NO-donor improved insulin secretion in the diabetic mice. After a chronic NO-donor treatment (1 week), we observe an improvement of GLP-1 sensitivity since GLP-1-induced insulin secretion was enhanced by the treatment. Interestingly, L-arginine could also improve another feature of the GLP-1-dependent enteric nervous system gut-brain axis that is gastric emptying. Conversely, the control of food intake by GLP-1, which does not only require the gut-brain axis, was not inhibited by NOS inhibitor or improved by the NO-donor treatment. To ascertain that GLP-1 directly increases NO production from enteric neurons, we incubated increasing doses of GLP-1 with primary culture of enteric neurons from NCD and HFD-fed, GLP-1-resistant mice. The enteric neurons from the HFD-fed mice were dramatically resistant to GLP-1-induced NO production. To validate that the GLP-1 resistance observed in primary culture of neurons from HFD-fed mice was also observed in vivo, we measured GLP-1-induced NO production ex vivo from ileum segments. GLP-1-induced NO production was similar between NCD and HC-HFD-fed GLP-1 sensitive mice while totally blunted in HFD-fed GLP-1 resistant mice further demonstrating the state of GLP-1 resistance of this animal model. The NO production was specific to the GLP-1 receptor since Exendin 9 prevented GLP-1 induced NO production. We here show that enteric NO production is a signaling molecule of GLP-1 for the control of GLP-1-regulated metabolic features and that this signaling pathway is impaired in HFD-fed mice. Altogether, these data clearly show that NO is an important mediator of the GLP-1 gut brain-dependent actions, which can improve GLP-1 sensitivity of HFD-diabetic mice. Numerous mechanisms could be at play and responsible for the impairment of NO production. NOSs are notably substrates of the AMP-activated kinase (Canabal et al., 2007; Han et al., 2012; Murphy et al., 2009) that is considered as a master molecular switch in energy sensing. Therefore, changes in intestinal energy metabolism, such as in response to a fat-enriched diet could be considered as a triggering mechanism of the AMP-activated kinase/NOS. The presence or absence of carbohydrate in the diet, as in our animal model, would be an important regulator since the phosphorylation of AMP-activated kinase is enhanced in case of impaired glucose availability (Sun et al., 2010). The change of diet could therefore initiate this pathway. On the other hand, HFD-induced inflammation can affect both pathways: AMP-activated kinase/NOS and Akt/NOS particularly in endothelial cells (Lee et al., 2014). Altogether, our present data show that the HFD-fed mouse model triggers GLP-1 resistance through a mechanism involving and impaired enteric NO production. The mechanism responsible for the impairment of GLP-1 receptor-mediated enteric NO production are unknown but could be related to high-fat diet-induced ileum microbiota dysbiosis as we previously showed dysbiosis (Everard et al., 2014; Garidou et al., 2015; Serino et al., 2012). Another regulator of intestinal energy metabolism and GLP-1 homeostasis is gut microbiota (Cani et al., 2008; Cani et al., 2007b). Furthermore, since HFD dramatically modifies the gut microbiota ecology, which varies according to individuals, we envisaged that a specific microbiota dysbiosis could be responsible for the specific GLP-1 resistance observed in the HFD-fed mice only.

Figure 1C:
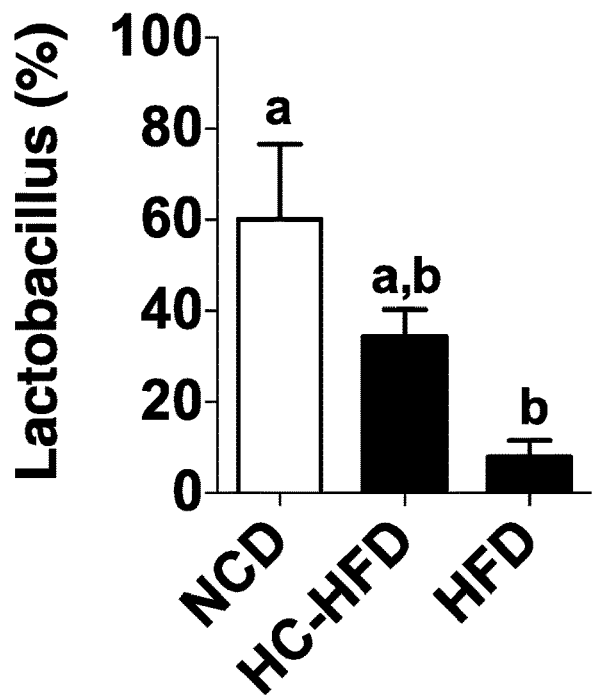

Gut microbiota dysbiosis is responsible for the GLP-1 resistance. In the quest for a cause to the impairment of GLP-1 sensitivity that was mediated by the reduced GLP-1-induced enteric NO production in response to a HFD, we studied the leading hypothesis of the control of glucose homeostasis i.e. the role of gut microbiota. We and others previously demonstrated that a fat-enriched diet induces gut microbiota dysbiosis (Everard et al., 2014; Garidou et al., 2015; Serino et al., 2012). Therefore, to identify bacterial taxons associated with GLP-1 resistance, we performed targeted 16S sequencing of the microbiota from the ileum of all animal models. We focused out attention on the ileum rather than caecum microbiota since GLP-1 producing cells are mostly located in the ileum of the mouse intestine. The discriminant analysis of differences as analyzed by LefSe showed taxonomic signatures specific for each mouse group. We then performed linear regression analyses on all taxonomic features and identified that the *Lactobacillus* genus from the lactobacillaceae family was tightly correlated with the ileum GLP-1r and nNOS mRNA concentrations (FIGS. 1A&B). These correlations are also observed at the family, class and order taxonomic levels. The frequency of *Lactobacillus* among the overall taxons was dramatically reduced in the ileum from the HFD-fed GLP-1-resistant mice while modestly reduced in the HC-HFD-fed GLP-1 sensitive mice (FIG. 1C). To demonstrate the causality of the role played by gut microbiota on GLP-1 resistance, we quantified GLP-1 resistance in germ free mice. The data showed that the absence of microbiota prevented from GLP-1-induced insulin secretion demonstrating a strong state of GLP-1 resistance. This impairment was associated with a lack of activation of the gut-brain axis since the number of cFos positive cells in the brain stem could not be increased by GLP-1 administration. The state of GLP-1 resistance in germ free mice is further supported by the fact that the plasma concentration of GLP-1 is dramatically higher than what observed in conventionalized mice, whereas plasma insulin concentration remain low. This was previously reported as well in other instances and shows that the overall GLP-1 physiology i.e. secretion and action is under the control of gut microbiota (Cani et al., 2007b; Nguyen et al., 2014; Tolhurst et al., 2012; Wichmann et al., 2013). Although the bacteria responsible for the control of GLP-1 action remain unknown, we here identified that the *Lactobacillus* genus could be a good candidate since the proportion of this taxon was highly correlated with GLP-1 receptor and nNOS mRNA concentrations. Our data is supported by the concept that *Lactobacillus* and *Bifidobacteria* are probiotics that could be suitable for metabolic management (Mekkes et al., 2014; Panwar et al., 2013). Recent data also show that in humans, *Lactobacillus reuturi* administration improves glucose-induced incretin and insulin secretion (Simon et al., 2015). The mechanism could be linked to the production of short chain fatty acids acetate, propionate, butyrate in the gut which, through GPR41/43 i.e. FFAR2/3, respectively, or LPS, through TLR4, could enhance GLP-1 secretion (Everard and Cani, 2014; Nguyen et al., 2014; Tolhurst et al., 2012). Other evidence show that the FFAR3 and TLRs are also expressed in the neuronal cells of the submucosal and myenteric ganglia suggesting that SCFA or LPS could directly trigger enteric neurons (Barajon et al., 2009; Nohr et al., 2013). Very convincing data show that acetate trigger insulin secretion through a parasympathetic gut-brain axis (Perry et al., 2016). However, a two months prebiotic treatment, which increases short chain fatty acid production (Garidou et al., 2015), did not restore GLP-1-induced insulin secretion, gastric emptying and food intake. Therefore, the mechanism has to be different from the production of short chain fatty acids by gut microbiota. The mechanism has to be NO-dependent, as show previously to be under the control of *Lactobacillus* which can modulate intestinal NO synthesis (Morita et al., 1997; Yarullina et al., 2016). We therefore, validated this hypothesis by studying the production of NO by enteric neurons from germ free mice and show that NO production could not be stimulated by GLP-1 demonstrating that gut microbiota is a required feature for the activation of the gut-brain axis by GLP-1 through the production of NO. Therefore, the mice were conventionalized for two weeks with the ileum microbiota from both HFD-fed mice and observed that GLP-1 resistance was only partially reversed. This data show that the microbiota ecology could not totally reversed the GLP-1 resistant state and was not able to program GLP-1 sensitivity. In addition, features of the enteric neurons, i.e. PGP9.5 and prph and enteric glial cells, i.e. GFAP and S100β were reduced in the ileum of germ free mice while mRNA concentrations of neuronal and glial markers were unchanged in the nodose ganglia. They were not improved by the conventionalization with the microbiota from any of the fat-enriched diet-fed mice showing that this feature was similarly requiring a eubiotic microbiota to be restored as in conventional mice. Furthermore, we quantified other features of GLP-1 sensitivity such as the ileum mRNA concentrations encoding the GLP-1 receptor and the nNOS and found that they were dramatically reduced in germ free mice. Interestingly, in the ileum, the mRNA concentration encoding for the GLP-1 receptor was increased in the germ free mice colonized with the microbiota from the HC-HFD-fed, GLP-1-sensitive mice but not when colonized with the microbiota from HFD-fed GLP-1 resistant mice, demonstrating that the type of microbiota controls GLP-1 mRNA expression. These modification is not observed for ileum mRNA of nNOS. We observe any difference of nodose ganglia GLP-1r and nNOS mRNA concentrations between all mice. Eventually, to further demonstrate the role of gut microbiota on GLP-1 resistance, we treated mice with antibiotics for one month. In such condition, the antibiotic treatment induced a strong GLP-1 resistance to insulin secretion in NCD fed mice suggesting that some beneficial microbes were responsible for the improvement of GLP-1 sensitivity. Importantly, the antibiotic treatment of fat-enriched diet-fed mice could conversely improve GLP-1 sensitivity suggesting that some deleterious bacteria from the dysbiotic microbiota were eliminated by the antibiotic treatment. The impact of antibiotics was also observed on neuron specific proteins PGP9.5 and glial specific proteins S100b. While the antibiotics reduced the expression of the corresponding gene expression in NCD-fed mice the treatment conversely increased the gene expression in fat-enriched diet-fed mice. For mRNA from nodose ganglion, we observe no difference of their concentrations except for GFAP mRNA: its concentration decreased in NCD-fed antibiotic-treated mice and increased in HFD-fed antibiotic-treated mice. Similar results were obtained for the GLP-1 receptor and for the nNOS mRNA concentrations in the ileum and the nodose ganglion: their concentrations decreased in NCD-fed antibiotic-treated mice and increased in HFD-fed antibiotic-treated mice. This last set of data strongly supports the notion that a eubiotic gut microbiota enhances GLP-1 sensitivity while a dysbiotic microbiota reduces it. The impact of antibiotics was not restricted to GLP-1-increased insulin secretion since we also observed an alteration of GLP-1-induced gastric emptying inhibition in NCD-fed, antibiotics-treated mice and an improvement of its in HC-HFD and HFD-fed, antibiotics-treated mice. Conversely, energy intake remained unaffected by antibiotics in HC-HFD and HFD mice while dramatically altered in antibiotic-treated NCD fed mice showing the importance of the maintenance of a eubiotic microbiota.

Altogether, changes in ileum microbiota, putatively through changes in Lactobacillus, was causally associated with changes in GLP-1 sensitivity for the activation of the gut-brain axis and notably the stimulation of insulin secretion. Nitric oxide is an important signaling molecule of GLP-1 signaling. Therefore, the mechanisms involved in the detection of gut microbiota dysbiosis could be involved in the control of GLP-1 action.

The Microbial Associated Molecular Pattern Receptors NOD2, CD14, and TLR4 Controls GLP-1 Sensitivity.

The mechanisms ensuring a normal GLP-1 physiology and gut-brain axis control could be related to the role played by the microbial associated molecular pattern receptor NOD2, TLR4 or CD14. We previously demonstrated that NOD2, CD14 and TLR4 were involved in the glycemic control in response to a high-fat diet (Cani et al., 2008; Cani et al., 2007b; Denou et al., 2015; Prajapati et al., 2014). Therefore, since our data demonstrate the importance of a change in gut microbiota on the control of GLP-1 sensitivity, we analyzed NOD2, CD14 and TLR4 knockout (KO) mice. The data show that GLP-1-induced insulin secretion was dramatically reduced in all KO mice when compared to wild type controls. However, in all KO mice, the downstream effectors of GLP-1 sensitivity such as the number of enteric neurons and glial cells, as assessed by the concentration of mRNA for PGP9.5, peripherin, GFAP and S100β, in the ileum and the nodose ganglion, and the mRNA concentrations encoding for the GLP-1 receptor and nNOS, remained similar to wild type mice. Gastric emptying was also impaired in the all KO mice while food intake remained unchanged. This set of data further reinforces the role played by gut microbiota on the control of GLP-1 induced insulin secretion and gastric emptying. We add to the knowledge that PRR signaling is important for the control of GLP-1 signaling.

Discussion:

Large clinical trials of GLP-1-based therapeutic strategies show that 45-60% of patients treated with DPP4 inhibitors and GLP-1 receptor agonists fail to reach target (Esposito et al., 2011) suggesting a state of GLP-1 resistance. We here identified in different mouse models of type 2 diabetes features of gut microbiota dysbiosis that putatively through the reduction of their frequency in the ileum Lactobacillus are responsible for GLP-1 unresponsiveness on enteric neurons. We identified that gut microbiota dysbiosis hampers GLP-1-induced NO production by enteric neurons that prevents an efficient activation of the gut-brain to periphery axis. Insulin secretion and gastric emptying are directly under the control of this mechanism while the control of food intake by GLP-1 is rather not. These observations could be the basis of precision medicine and for novel therapeutic strategies targeting gut NO physiology or microbiota.

Incretin based therapeutic strategies control glycemia through a direct effect of GLP-1 on the insulin secreting beta cells and an indirect effect through the recruitment of the gut to brain to periphery axis. Therefore, mechanisms of GLP-1 resistance could hamper both modes of action. The respective contribution of each pathway is unknown but GLP-1 unresponsiveness was suggested in diabetic patients with neuropathy (Delgado-Aros et al., 2003; Lobinet et al., 2015) and vagal GLP-1r is essential for the control of insulin secretion and gastric emptying (Krieger et al., 2016), as we here observed. Furthermore, the efficacy of the therapeutic strategy varies according to the individuals. Therefore, to identify mechanisms responsible for the sensitivity of an individual patient to a given incretin-based strategy, there is a need for a concept that could encompass the susceptibility of each individual to develop a metabolic disease with the multiple etiology of the disease. The discovery of the major impact of gut microbiota on metabolic disease, of its diversity, and that type 2 diabetic patients are characterized by a gut microbiota dysbiosis is opening opportunities to gain knowledge about the mechanisms of GLP-1 resistance or unresponsiveness (Amar et al., 2008; Backhed et al., 2004; Cani et al., 2007a; Cani et al., 2008; Ley et al., 2005; Turnbaugh et al., 2006).

We here brought the first evidence that a specific gut microbiota is associated with GLP-1 unresponsiveness that affects the gut-brain to beta cell axis. The reduced frequency of the Lactobacillus genus was the most evident features of gut microbiota dysbiosis explaining GLP-1 resistance. In healthy situation, a first molecular mechanism responsible for GLP-1 sensitivity would be the capacity of Lactobacillus to ferment complex carbohydrate into short chain fatty acids (Cani et al., 2007b; De Vadder et al., 2014; Everard and Cani, 2014; Nohr et al., 2013; Perry et al., 2016; Tolhurst et al., 2012). However, we ruled out this hypothesis since the changes in short chain fatty acids observed in prebiotic treated mice don't improve the GLP-1 responsivness. A second mechanism would be that Lactobacillus are recognized by molecular pattern recognition receptors such as nucleotide-binding oligomerization domain receptors 1&2 which could regulate inflammation in the gut. We explored this second avenue and show that NOD2 is required to ensure GLP-1-induced insulin secretion. NOD2 recognizes peptidoglycan motifs from the bacterial cell wall that consists of N-acetylglucosamine and N-acetylmuramic acid. Precisely, NOD2 receptor can sense intracellular muramyl dipeptide (MDP), typical for gram positive bacteria such as Lactobacillus that regulate intestinal inflammation homeostasis (Kozakova et al., 2016; Macho Fernandez et al., 2011). Linked to that mechanism Lactobacillus could controls the availability of NO in the gut (Morita et al., 1997; Yarullina et al., 2016). Numerous other bacteria-related molecules are detected by the host and influence GLP-1 physiology such as short chain fatty acid/FFAR (Cani et al., 2007b; Tolhurst et al., 2012), LPS/TLR4 (Nguyen et al., 2014) or indole (Chimerel et al., 2014). Intestinal microbiota and its specific receptor (TLR, FFAR) are also important to regulate functions under the control of the enteric nervous system such as intestinal transit (Anitha et al., 2012; Brun et al., 2013; Kabouridis et al., 2015; Nohr et al., 2013; Wichmann et al., 2013) and gut-brain axis (De Vadder et al., 2014; Mayer et al., 2015). In this context, we observe that CD14/TLR4 could be important receptors to control GLP-1 sensitivity in mice. Such functions could be mediated by Lactobacillus and notably through GLP-1 secretion (Simon et al., 2015) on intestinal NO production and on the control of intestinal transit (Morita et al., 1997; Yarullina et al., 2016).

Another hypothesis is that the pro and anti-inflammatory cytokines issued from the gut microbiota dysbiosis to host crosstalk would regulate glucose and GLP-1 effectiveness of the beta cell (Green et al., 2016; Varin et al., 2016). The molecular mechanisms of GLP-1 resistance could be linked to the down regulation and the desensitization of the GLP-1 receptor (Baggio et al., 2004; Widmann et al., 1997) that will reduce the production of secondary messengers such as cAMP, and nitric oxide in different cell types (Cabou et al., 2011; Ding and Zhang, 2012; Drucker et al., 1987; Farina et al., 2003; Liu et al., 2015; Rotondo et al., 2011). In the intestine, the GLP-1 receptor is localized mainly on nNOS positive neurons (Richards et al., 2014). In animal models of type 2 diabetes or in diabetic patients, a reduced number of GLP-1 receptor at the surface of βcells and hypothalamic neuronal cell has been observed that was induced by hyperglycemia and hyperlipidemia (Burcelin et al., 2009; Hodson et al., 2013; Ten Kulve et al., 2015; Xu et al., 2007; Yang et al., 2016; Younan and Rashed, 2007) that could hamper NO production. In human, the NO-donor L-arginine improves meal-induced insulin secretion when administered orally in healthy, type II diabetic patients, and diabetic mice (Ozbek et al., 2009; Tang et al., 2013). Our results show that acute and chronic NO treatment in type II diabetic mice restore the GLP-1 sensitivity for insulin secretion and gastric emptying. Therefore, we suggest that a reduced GLP-1 receptor signaling for the production of NO could exist in the enteric nervous system in response to gut microbiota dysbiosis as induced by a fat-enriched diet. This hypothesis is supported by the following results. We observed that NO production by neurons is required to mediate the effect of GLP-1 on the gut-brain-periphery axis. It is strongly reduced in type 2 diabetic models as well as in germ free mice. Importantly, it was shown that germ-free mice are characterized by enteric and neuronal atrophy. Conventionalization restores the neuronal function (McVey Neufeld et al., 2015). We also observed a state of neuropathy in type 2 diabetic mice as evidenced by the reduced number of neurons and neuronal proteins of the enteric nervous system showing the importance of microbiota on the healthy development of the gut brain axis, as reported in other instances (Ochoa-Reparaz and Kasper, 2016).

In conclusion, we here show that in subsets of high-fat diet fed mice with type 2 diabetes a specific gut microbiota dysbiosis hampers GLP-1-induced nitric oxide production through a NOD2/TLR4/CD14-dependant mechanism preventing hence the activation of the gut-brain axis for the control of insulin-secretion.

EXAMPLE 2

Experimental Procedure

Mice are fed during three months with HFD (high-fat high-carbohydrate diet). *Lactobacilli* are given daily by gavage (109/mouse) during 1-1.5 months and after 2 months of diet. Quantification of the glycemic control i.e. intravenous glucose tolerance test and quantification of the glycemic profile and of the plasma insulin concentrations 15 minutes after the glycemic challenge.

Primary criteria: An improvement of the glucose control by the GLP-1 receptor agonist when the mice have been pretreated with the *Lactobacilli* strategy.

Secondary criteria: a change in plasma insulin secretion.
Results

Figure 2A:
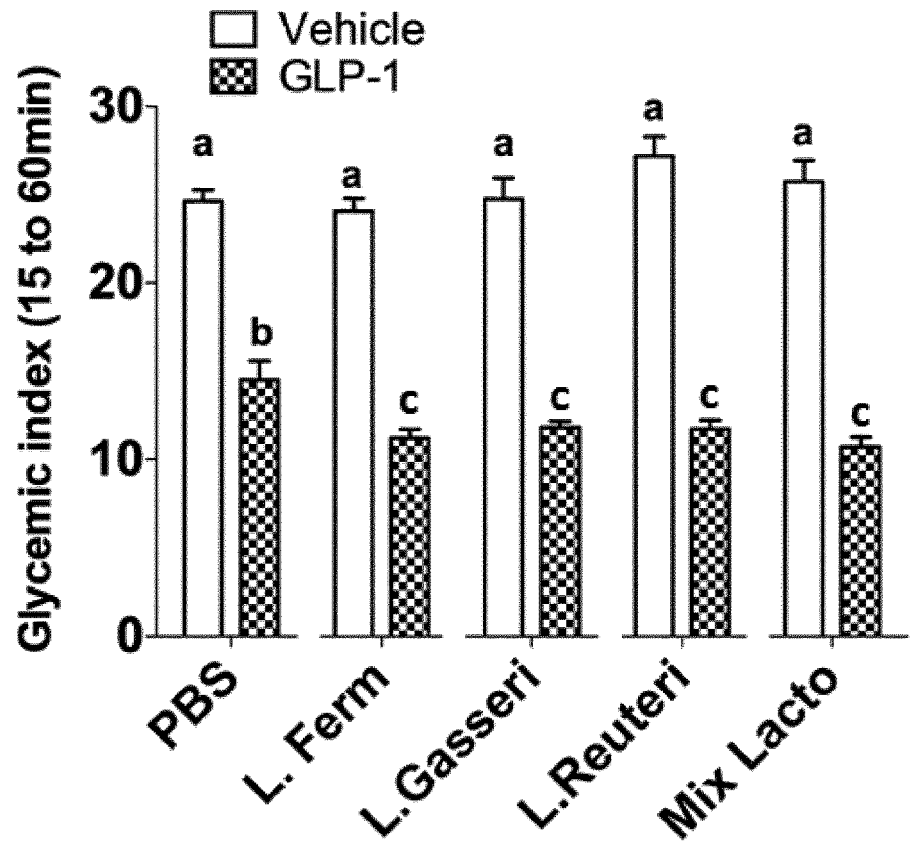
Figure 2B:
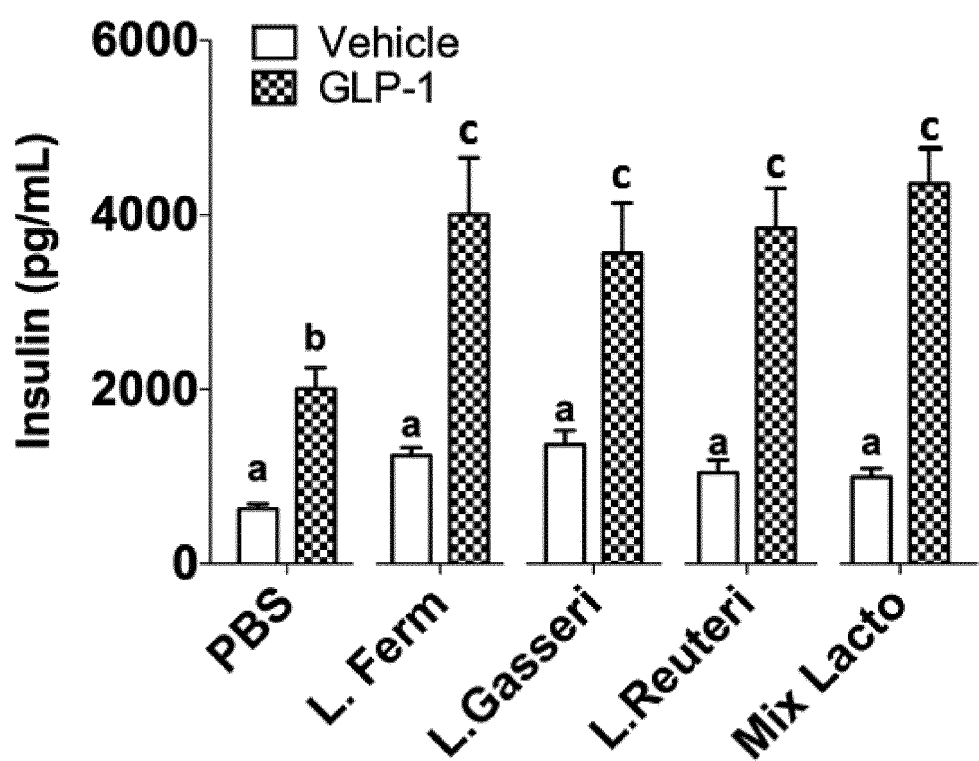

The data show that the chronic treatment of the type 2 diabetic mice with a *Lactobacilli* (any one!) improves the quality of the glucose control by the GLP-1 receptor agonist (natural GLP-1 molecule) since in absence of GLP-1 the *Lactobacilli* treatment does not have an impact on itself. Therefore, it looks that the use of any *Lactobacilli* is reaching the primary criteria only when associated with the GLP-1 agonist (FIG. 2A). The second criteria is i.e. concerning the mode of action is also reached i.e. insulin secretion in response to the GLP-1 receptor agonist is increased when the diabetic mice are simultaneously treated with the *Lactobacilli* treatment (FIG. 2B). Therefore, this is most likely the mode of action of the *Lactobacilli* for the improvement of the glucose control induced by the GLP-1 receptor agonist.

REFERENCES

Throughout this application, various references describe the state of the art to which this invention pertains. The disclosures of these references are hereby incorporated by reference into the present disclosure.

Amar, J., Burcelin, R., Ruidavets, J. B., Cani, P. D., Fauvel, J., Alessi, M. C., Chamontin, B., and Ferrieres, J. (2008). Energy intake is associated with endotoxemia in apparently healthy men. Am J Clin Nutr 87, 1219-1223.

Amato, A., Cinci, L., Rotondo, A., Serio, R., Faussone-Pellegrini, M. S., Vannucchi, M. G., and Mule, F. (2010). Peripheral motor action of glucagon-like peptide-1 through enteric neuronal receptors. Neurogastroenterol Motil 22, 664-e203.

Anitha, M., Gondha, C., Sutliff, R., Parsadanian, A., Mwangi, S., Sitaraman, S. V., and Srinivasan, S. (2006). GDNF rescues hyperglycemia-induced diabetic enteric neuropathy through activation of the PI3K/Akt pathway. The Journal of clinical investigation 116, 344-356.

Anitha, M., Vijay-Kumar, M., Sitaraman, S. V., Gewirtz, A. T., and Srinivasan, S. (2012). Gut microbial products regulate murine gastrointestinal motility via Toll-like receptor 4 signaling. Gastroenterology 143, 1006-1016 e1004.

Backhed, F., Ding, H., Wang, T., Hooper, L. V., Koh, G. Y., Nagy, A., Semenkovich, C. F., and Gordon, J. I. (2004). The gut microbiota as an environmental factor that regulates fat storage. Proc Natl Acad Sci USA 101, 15718-15723.

Baggio, L. L., Kim, J. G., and Drucker, D. J. (2004). Chronic exposure to GLP-1R agonists promotes homologous GLP-1 receptor desensitization in vitro but does not attenuate GLP-1R-dependent glucose homeostasis in vivo. Diabetes 53 Suppl 3, S205-214.

Barajon, I., Serrao, G., Arnaboldi, F., Opizzi, E., Ripamonti, G., Balsari, A., and Rumio, C. (2009). Toll-like receptors 3, 4, and 7 are expressed in the enteric nervous system and dorsal root ganglia. J Histochem Cytochem 57, 1013-1023.

Baumgartner, I., Pacheco-Lopez, G., Ruttimann, E. B., Arnold, M., Asarian, L., Langhans, W., Geary, N., and Hillebrand, J. J. (2010). Hepatic-portal vein infusions of glucagon-like peptide-1 reduce meal size and increase c-Fos expression in the nucleus tractus solitarii, area postrema and central nucleus of the amygdala in rats. J Neuroendocrinol 22, 557-563.

Brun, P., Giron, M. C., Qesari, M., Porzionato, A., Caputi, V., Zoppellaro, C., Banzato, S., Grillo, A. R., Spagnol, L., De Caro, R., et al. (2013). Toll-like receptor 2 regulates intestinal inflammation by controlling integrity of the enteric nervous system. Gastroenterology 145, 1323-1333.

Burcelin, R., Crivelli, V., Dacosta, A., Roy-Tirelli, A., and Thorens, B. (2002). Heterogeneous metabolic adaptation of C57BL/6J mice to high-fat diet. Am J Physiol Endocrinol Metab 282, E834-842.

Burcelin, R., Da Costa, A., Drucker, D., and Thorens, B. (2001). Glucose competence of the hepatoportal vein sensor requires the presence of an activated glucagon-like peptide-1 receptor. Diabetes 50, 1720-1728.

Burcelin, R., Dolci, W., and Thorens, B. (2000). Glucose sensing by the hepatoportal sensor is GLUT2-dependent: in vivo analysis in GLUT2-null mice. Diabetes 49, 1643-1648.

Burcelin, R., Serino, M., and Cabou, C. (2009). A role for the gut-to-brain GLP-1-dependent axis in the control of metabolism. Curr Opin Pharmacol 9, 744-752.

Cabou, C., Vachoux, C., Campistron, G., Drucker, D. J., and Burcelin, R. (2011). Brain GLP-1 signaling regulates femoral artery blood flow and insulin sensitivity through hypothalamic PKC-delta. Diabetes 60, 2245-2256.

Canabal, D. D., Song, Z., Potian, J. G., Beuve, A., McArdle, J. J., and Routh, V. H. (2007). Glucose, insulin, and leptin signaling pathways modulate nitric oxide synthesis in glucose-inhibited neurons in the ventromedial hypothalamus. Am J Physiol Regul Integr Comp Physiol 292, R1418-1428.

Cani, P. D., Amar, J., Iglesias, M. A., Poggi, M., Knauf, C., Bastelica, D., Neyrinck, A. M., Fava, F., Tuohy, K. M., Chabo, C., et al. (2007a). Metabolic endotoxemia initiates obesity and insulin resistance. Diabetes 56, 1761-1772.

Cani, P. D., Bibiloni, R., Knauf, C., Waget, A., Neyrinck, A. M., Delzenne, N. M., and Burcelin, R. (2008). Changes in gut microbiota control metabolic endotoxemia-induced inflammation in high-fat diet-induced obesity and diabetes in mice. Diabetes 57, 1470-1481.

Cani, P. D., Hoste, S., Guiot, Y., and Delzenne, N. M. (2007b). Dietary non-digestible carbohydrates promote L-cell differentiation in the proximal colon of rats. Br J Nutr 98, 32-37.

Chimerel, C., Emery, E., Summers, D. K., Keyser, U., Gribble, F. M., and Reimann, F. (2014). Bacterial metabolite indole modulates incretin secretion from intestinal enteroendocrine L cells. Cell Rep9, 1202-1208.

Dalle, S., Burcelin, R., and Gourdy, P. (2013). Specific actions of GLP-1 receptor agonists and DPP4 inhibitors for the treatment of pancreatic beta-cell impairments in type 2 diabetes. Cell Signal 25, 570-579.

De Vadder, F., Kovatcheva-Datchary, P., Goncalves, D., Vinera, J., Zitoun, C., Duchampt, A., Backhed, F., and Mithieux, G. (2014). Microbiota-generated metabolites promote metabolic benefits via gut-brain neural circuits. Cell 156, 84-96.

Delgado-Aros, S., Vella, A., Camilleri, M., Low, P. A., Burton, D. D., Thomforde, G. M., and Stephens, D. (2003). Effects of glucagon-like peptide-1 and feeding on gastric volumes in diabetes mellitus with cardio-vagal dysfunction. Neurogastroenterol Motil 15, 435-443.

Denou, E., Lolmede, K., Garidou, L., Pomie, C., Chabo, C., Lau, T. C., Fullerton, M. D., Nigro, G., Zakaroff-Girard, A., Luche, E., et al. (2015). Defective NOD2 peptidoglycan sensing promotes diet-induced inflammation, dysbiosis, and insulin resistance. EMBO Mol Med 7, 259-274.

Ding, L., and Zhang, J. (2012). Glucagon-like peptide-1 activates endothelial nitric oxide synthase in human umbilical vein endothelial cells. Acta Pharmacol Sin 33, 75-81.

Drucker, D. J., Philippe, J., Mojsov, S., Chick, W. L., and Habener, J. F. (1987). Glucagon-like peptide I stimulates insulin gene expression and increases cyclic AMP levels in a rat islet cell line. Proc Natl Acad Sci USA 84, 3434-3438.

Duca, F. A., Cote, C. D., Rasmussen, B. A., Zadeh-Tahmasebi, M., Rutter, G. A., Filippi, B. M., and Lam, T. K. (2015). Metformin activates a duodenal Ampk-dependent pathway to lower hepatic glucose production in rats. Nat Med 21, 506-511.

Esposito, K., Mosca, C., Brancario, C., Chiodini, P., Ceriello, A., and Giugliano, D. (2011). GLP-1 receptor agonists and HBAlc target of <7% in type 2 diabetes: meta-analysis of randomized controlled trials. Curr Med Res Opin 27, 1519-1528.

Everard, A., Belzer, C., Geurts, L., Ouwerkerk, J. P., Druart, C., Bindels, L. B., Guiot, Y., Derrien, M., Muccioli, G. G., Delzenne, N. M., et al. (2013). Cross-talk between Akkermansia muciniphila and intestinal epithelium controls diet-induced obesity. Proc Natl Acad Sci USA 110, 9066-9071.

Everard, A., and Cani, P. D. (2014). Gut microbiota and GLP-1. Rev Endocr Metab Disord 15, 189-196.

Everard, A., Lazarevic, V., Gaia, N., Johansson, M., Stahlman, M., Backhed, F., Delzenne, N. M., Schrenzel, J., Francois, P., and Cani, P. D. (2014). Microbiome of prebiotic-treated mice reveals novel targets involved in host response during obesity. ISME J 8, 2116-2130.

Farilla, L., Bulotta, A., Hirshberg, B., Li Calzi, S., Khoury, N., Noushmehr, H., Bertolotto, C., Di Mario, U., Harlan, D. M., and Perfetti, R. (2003). Glucagon-like peptide 1 inhibits cell apoptosis and improves glucose responsiveness of freshly isolated human islets. Endocrinology 144, 5149-5158.

Forslund, K., Hildebrand, F., Nielsen, T., Falony, G., Le Chatelier, E., Sunagawa, S., Prifti, E., Vieira-Silva, S., Gudmundsdottir, V., Krogh Pedersen, H., et al. (2015). Disentangling type 2 diabetes and metformin treatment signatures in the human gut microbiota. Nature 528, 262-266.

Fournel, A., Drougard, A., Duparc, T., Marlin, A., Brierley, S. M., Castro, J., Le-Gonidec, S., Masri, B., Colom, A., Lucas, A., et al. (2015). Apelin targets gut contraction to control glucose metabolism via the brain. Gut.

Franklin, K. B. J., and Paxinos, G. (1997). The mouse brain in stereotaxic coordinates. (San Diego: Academic Press).

Fujiwara, K., Gotoh, K., Chiba, S., Masaki, T., Katsuragi, I., Kakuma, T., and Yoshimatsu, H. (2012). Intraportal administration of DPP-IV inhibitor regulates insulin secretion and food intake mediated by the hepatic vagal afferent nerve in rats. J Neurochem 121, 66-76.

Garidou, L., Pomie, C., Klopp, P., Waget, A., Charpentier, J., Aloulou, M., Giry, A., Serino, M., Stenman, L., Lahtinen, S., et al. (2015). The Gut Microbiota Regulates Intestinal CD4 T Cells Expressing RORgammat and Controls Metabolic Disease. Cell Metab 22, 100-112.

George, A. M., Jacob, A. G., and Fogelfeld, L. (2015). Lean diabetes mellitus: An emerging entity in the era of obesity. World J Diabetes 6, 613-620.

Gill, S. R., Pop, M., Deboy, R. T., Eckburg, P. B., Turnbaugh, P. J., Samuel, B. S., Gordon, J. I., Relman, D. A., Fraser-Liggett, C. M., and Nelson, K. E. (2006). Metagenomic analysis of the human distal gut microbiome. Science 312, 1355-1359.

Green, A. D., Vasu, S., Moffett, R. C., and Flatt, P. R. (2016). Co-culture of clonal beta cells with GLP-1 and glucagon-secreting cell line impacts on beta cell insulin secretion, proliferation and susceptibility to cytotoxins. Biochimie 125, 119-125.

Han, L., Yu, Y., Sun, X., and Wang, B. (2012). Exendin-4 directly improves endothelial dysfunction in isolated aortas from obese rats through the cAMP or AMPK-eNOS pathways. Diabetes Res Clin Pract 97, 453-460.

Hansen, L., Deacon, C. F., Orskov, C., and Holst, J. J. (1999). Glucagon-like peptide-1-(7-36)amide is transformed to glucagon-like peptide-1-(9-36)amide by dipeptidyl peptidase IV in the capillaries supplying the L cells of the porcine intestine. Endocrinology 140, 5356-5363.

Hodson, D. J., Mitchell, R. K., Bellomo, E. A., Sun, G., Vinet, L., Meda, P., Li, D., Li, W. H., Bugliani, M., Marchetti, P., et al. (2013). Lipotoxicity disrupts incretin-regulated human beta cell connectivity. The Journal of clinical investigation 123, 4182-4194.

Holst, J. J. (2007). The physiology of glucagon-like peptide 1. Physiol Rev 87, 1409-1439.

Imeryuz, N., Yegen, B. C., Bozkurt, A., Coskun, T., Villanueva-Penacarrillo, M. L., and Ulusoy, N. B. (1997). Glucagon-like peptide-1 inhibits gastric emptying via vagal afferent-mediated central mechanisms. Am J Physiol 273, G920-927.

Ishii, M., Shibata, R., Kondo, K., Kambara, T., Shimizu, Y., Tanigawa, T., Bando, Y. K., Nishimura, M., Ouchi, N., and Murohara, T. (2014). Vildagliptin stimulates endothelial cell network formation and ischemia-induced revascularization via an endothelial nitric-oxide synthase-dependent mechanism. J Biol Chem 289, 27235-27245.

Kabouridis, P. S., Lasrado, R., McCallum, S., Chng, S. H., Snippert, H. J., Clevers, H., Pettersson, S., and Pachnis, V. (2015). Microbiota controls the homeostasis of glial cells in the gut lamina propria. Neuron 85, 289-295.

Kozakova, H., Schwarzer, M., Tuckova, L., Srutkova, D., Czarnowska, E., Rosiak, I., Hudcovic, T., Schabussova, I., Hermanova, P., Zakostelska, Z., et al. (2016). Colonization of germ-free mice with a mixture of three *Lactobacillus* strains enhances the integrity of gut mucosa and ameliorates allergic sensitization. Cell Mol Immunol 13, 251-262.

Krieger, J. P., Arnold, M., Pettersen, K. G., Lossel, P., Langhans, W., and Lee, S. J. (2016). Knockdown of GLP-1 Receptors in Vagal Afferents Affects Normal Food Intake and Glycemia. Diabetes 65, 34-43.

Krieger, J. P., Langhans, W., and Lee, S. J. (2015). Vagal mediation of GLP-1's effects on food intake and glycemia. Physiol Behav 152, 372-380.

Landowski, L. M., Dyck, P. J., Engelstad, J., and Taylor, B. V. (2016). Axonopathy in peripheral neuropathies: Mechanisms and therapeutic approaches for regeneration. J Chem Neuroanat.

Lee, C. H., Lee, S. D., Ou, H. C., Lai, S. C., and Cheng, Y. J. (2014). Eicosapentaenoic acid protects against palmitic acid-induced endothelial dysfunction via activation of the AMPK/eNOS pathway. Int J Mol Sci 15, 10334-10349.

Lee, J., Cummings, B. P., Martin, E., Sharp, J. W., Graham, J. L., Stanhope, K. L., Havel, P. J., and Raybould, H. E. (2012). Glucose sensing by gut endocrine cells and activation of the vagal afferent pathway is impaired in a rodent model of type 2 diabetes mellitus. Am J Physiol Regul Integr Comp Physiol 302, R657-666.

Ley, R. E., Backhed, F., Turnbaugh, P., Lozupone, C. A., Knight, R. D., and Gordon, J. I. (2005). Obesity alters gut microbial ecology. Proc Natl Acad Sci USA 102, 11070-11075.

Li, P. C., Liu, L. F., Jou, M. J., and Wang, H. K. (2016). The GLP-1 receptor agonists exendin-4 and liraglutide alleviate oxidative stress and cognitive and micturition deficits induced by middle cerebral artery occlusion in diabetic mice. BMC Neurosci 17, 37.

Liu, L., Liu, J., and Huang, Y. (2015). Protective Effects of Glucagon-like Peptide 1 on Endothelial Function in Hypertension. J Cardiovasc Pharmacol 65, 399-405.

Lobinet, E., Reichardt, F., Garret, C., Cazals, L., Waget, A., Dejager, S., Labrousse, F., Senard, J. M., Holst, J. J., Hanaire, H., et al. (2015). Autonomic Diabetic Neuropathy Impairs Glucose and Dipeptidyl Peptidase 4 Inhibitor-Regulated Glucagon Concentration in Type 1 Diabteci Patients. Journal of Endocrinolgy and Metabolism 5, 229-237.

Macho Fernandez, E., Valenti, V., Rockel, C., Hermann, C., Pot, B., Boneca, I. G., and Grangette, C. (2011). Anti-inflammatory capacity of selected *Lactobacilli* in experimental colitis is driven by NOD2-mediated recognition of a specific peptidoglycan-derived muropeptide. Gut 60, 1050-1059.

Mayer, E. A., Tillisch, K., and Gupta, A. (2015). Gut/brain axis and the microbiota. The Journal of clinical investigation 125, 926-938.

McVey Neufeld, K. A., Perez-Burgos, A., Mao, Y. K., Bienenstock, J., and Kunze, W. A. (2015). The gut microbiome restores intrinsic and extrinsic nerve function in germ-free mice accompanied by changes in calbindin. Neurogastroenterol Motil 27, 627-636.

Mekkes, M. C., Weenen, T. C., Brummer, R. J., and Claassen, E. (2014). The development of probiotic treatment in obesity: a review. Benef Microbes 5, 19-28.

Moore, P. C., Ugas, M. A., Hagman, D. K., Parazzoli, S. D., and Poitout, V. (2004). Evidence against the involvement of oxidative stress in fatty acid inhibition of insulin secretion. Diabetes 53, 2610-2616.

Morita, H., Yoshikawa, H., Sakata, R., Nagata, Y., and Tanaka, H. (1997). Synthesis of nitric oxide from the two equivalent guanidino nitrogens of L-arginine by *Lactobacillus fermentum*. J Bacteriol 179, 7812-7815.

Murphy, B. A., Fakira, K. A., Song, Z., Beuve, A., and Routh, V. H. (2009). AMP-activated protein kinase and nitric oxide regulate the glucose sensitivity of ventromedial hypothalamic glucose-inhibited neurons. Am J Physiol Cell Physiol 297, C750-758.

Nguyen, A. T., Mandard, S., Dray, C., Deckert, V., Valet, P., Besnard, P., Drucker, D. J., Lagrost, L., and Grober, J. (2014). Lipopolysaccharides-mediated increase in glucose-stimulated insulin secretion: involvement of the GLP-1 pathway. Diabetes 63, 471-482.

Nishizawa, M., Nakabayashi, H., Uehara, K., Nakagawa, A., Uchida, K., and Koya, D. (2013). Intraportal GLP-1 stimulates insulin secretion predominantly through the hepatoportal-pancreatic vagal reflex pathways. Am J Physiol Endocrinol Metab 305, E376-387.

Nohr, M. K., Pedersen, M. H., Gille, A., Egerod, K. L., Engelstoft, M. S., Husted, A. S., Sichlau, R. M., Grunddal, K. V., Poulsen, S. S., Han, S., et al. (2013). GPR41/FFAR3 and GPR43/FFAR2 as cosensors for short-chain fatty acids in enteroendocrine cells vs FFAR3 in enteric neurons and FFAR2 in enteric leukocytes. Endocrinology 154, 3552-3564.

Ochoa-Reparaz, J., and Kasper, L. H. (2016). The Second Brain: Is the Gut Microbiota a Link Between Obesity and Central Nervous System Disorders? Curr Obes Rep 5, 51-64.

Ozbek, M., Erdogan, M., Karadeniz, M., Cetinkalp, S., Ozgen, A. G., Saygili, F., Yilmaz, C., and Tuzun, M. (2009). Evaluation of beta cell dysfunction by mixed meal tolerance test and oral L-arginine in patients with newly diagnosed type 2 diabetes mellitus. Exp Clin Endocrinol Diabetes 117, 573-576.

Panwar, H., Rashmi, H. M., Batish, V. K., and Grover, S. (2013). Probiotics as potential biotherapeutics in the management of type 2 diabetes—prospects and perspectives. Diabetes Metab Res Rev 29, 103-112.

Perry, R. J., Peng, L., Barry, N. A., Cline, G. W., Zhang, D., Cardone, R. L., Petersen, K. F., Kibbey, R. G., Goodman, A. L., and Shulman, G. I. (2016). Acetate mediates a microbiome-brain-beta-cell axis to promote metabolic syndrome. Nature 534, 213-217.

Plamboeck, A., Veedfald, S., Deacon, C. F., Hartmann, B., Wettergren, A., Svendsen, L. B., Meisner, S., Hovendal, C., Knop, F. K., Vilsboll, T., et al. (2013). Characterisation of oral and i.v. glucose handling in truncally vagotomised subjects with pyloroplasty. Eur J Endocrinol 169, 187-201.

Poitout, V., and Robertson, R. P. (2008). Glucolipotoxicity: fuel excess and beta-cell dysfunction. Endocr Rev 29, 351-366.

Prajapati, B., Jena, P. K., Rajput, P., Purandhar, K., and Seshadri, S. (2014). Understanding and modulating the Toll like Receptors (TLRs) and NOD like Receptors (NLRs) cross talk in type 2 diabetes. Curr Diabetes Rev 10, 190-200.

Pujadas, G., De Nigris, V., La Sala, L., Testa, R., Genovese, S., and Ceriello, A. (2015). The pivotal role of high glucose-induced overexpression of PKCbeta in the appearance of glucagon-like peptide-1 resistance in endothelial cells. Endocrine.

Qin, J., Li, Y., Cai, Z., Li, S., Zhu, J., Zhang, F., Liang, S., Zhang, W., Guan, Y., Shen, D., et al. (2012). A metagenome-wide association study of gut microbiota in type 2 diabetes. Nature 490, 55-60.

Richards, P., Parker, H. E., Adriaenssens, A. E., Hodgson, J. M., Cork, S. C., Trapp, S., Gribble, F. M., and Reimann, F. (2014). Identification and characterization of GLP-1 receptor-expressing cells using a new transgenic mouse model. Diabetes 63, 1224-1233.

Rotondo, A., Amato, A., Lentini, L., Baldassano, S., and Mule, F. (2011). Glucagon-like peptide-1 relaxes gastric antrum through nitric oxide in mice. Peptides 32, 60-64.

Ruttimann, E. B., Arnold, M., Hillebrand, J. J., Geary, N., and Langhans, W. (2009). Intrameal hepatic portal and intraperitoneal infusions of glucagon-like peptide-1 reduce spontaneous meal size in the rat via different mechanisms. Endocrinology 150, 1174-1181.

Sato, J., Kanazawa, A., Ikeda, F., Yoshihara, T., Goto, H., Abe, H., Komiya, K., Kawaguchi, M., Shimizu, T., Ogihara, T., et al. (2014). Gut dysbiosis and detection of "live gut bacteria" in blood of Japanese patients with type 2 diabetes. Diabetes Care 37, 2343-2350.

Serino, M., Luche, E., Gres, S., Baylac, A., Berge, M., Cenac, C., Waget, A., Klopp, P., Iacovoni, J., Klopp, C., et al. (2012). Metabolic adaptation to a high-fat diet is associated with a change in the gut microbiota. Gut 61, 543-553.

Simon, M. C., Strassburger, K., Nowotny, B., Kolb, H., Nowotny, P., Burkart, V., Zivehe, F., Hwang, J. H., Stehle, P., Pacini, G., et al. (2015). Intake of *Lactobacillus reuteri* improves incretin and insulin secretion in glucose-tolerant humans: a proof of concept. Diabetes Care 38, 1827-1834.

Smith, T. H., Ngwainmbi, J., Grider, J. R., Dewey, W. L., and Akbarali, H. I. (2013). An in-vitro preparation of isolated enteric neurons and glia from the myenteric plexus of the adult mouse. J Vis Exp.

Stenkamp-Strahm, C. M., Kappmeyer, A. J., Schmalz, J. T., Gericke, M., and Balemba, O. (2013). High-fat diet ingestion correlates with neuropathy in the duodenum myenteric plexus of obese mice with symptoms of type 2 diabetes. Cell Tissue Res 354, 381-394.

Sun, G., Tarasov, A. I., McGinty, J., McDonald, A., da Silva Xavier, G., Gorman, T., Marley, A., French, P. M., Parker, H., Gribble, F., et al. (2010). Ablation of AMP-activated protein kinase alpha1 and alpha2 from mouse pancreatic beta cells and RIP2.Cre neurons suppresses insulin release in vivo. Diabetologia 53, 924-936.

Tang, Z. Q., Wu, T., Cui, S. W., Zhu, X. H., Yin, T., Wang, C. F., Zhu, J. Y., and Wu, A. J. (2013). Stimulation of insulin secretion by large-dose oral arginine administration in healthy adults. Exp Ther Med 6, 248-252.

Ten Kulve, J. S., van Bloemendaal, L., Balesar, R., R G, I. J., Swaab, D. F., Diamant, M., la Fleur, S. E., and Alkemade, A. (2015). Decreased hypothalamic glucagon-like peptide-1 receptor expression in type 2 diabetes patients. J Clin Endocrinol Metab, jc20153291.

Tolessa, T., Gutniak, M., Holst, J. J., Efendic, S., and Hellstrom, P. M. (1998). Glucagon-like peptide-1 retards gastric emptying and small bowel transit in the rat: effect mediated through central or enteric nervous mechanisms. Dig Dis Sci 43, 2284-2290.

Tolhurst, G., Heffron, H., Lam, Y. S., Parker, H. E., Habib, A. M., Diakogiannaki, E., Cameron, J., Grosse, J., Reimann, F., and Gribble, F. M. (2012). Short-chain fatty acids stimulate glucagon-like peptide-1 secretion via the G-protein-coupled receptor FFAR2. Diabetes 61, 364-371.

Toyoda, M., Yokoyama, H., Abe, K., Nakamura, S., and Suzuki, D. (2014). Predictors of response to liraglutide in Japanese type 2 diabetes. Diabetes Res Clin Pract 106, 451-457.

Turnbaugh, P. J., Ley, R. E., Mahowald, M. A., Magrini, V., Mardis, E. R., and Gordon, J. I. (2006). An obesity-associated gut microbiome with increased capacity for energy harvest. Nature 444, 1027-1031.

Varin, E. M., Wojtusciszyn, A., Broca, C., Muller, D., Ravier, M. A., Ceppo, F., Renard, E., Tanti, J. F., and Dalle, S. (2016). Inhibition of the MAP3 kinase Tpl2 protects rodent and human beta-cells from apoptosis and dysfunction induced by cytokines and enhances anti-inflammatory actions of exendin-4. Cell Death Dis 7, e2065.

Veedfald, S., Hansen, M., Christensen, L. W., Larsen, S. A., Hjollund, K. R., Plamboeck, A., Hartmann, B., Deacon, C. F., and Holst, J. J. (2016). The insulinotropic effect of exogenous GLP-1 is not affected by acute vagotomy in anaesthetized pigs. Exp Physiol.

Waget, A., Cabou, C., Masseboeuf, M., Cattan, P., Armanet, M., Karaca, M., Castel, J., Garret, C., Payros, G., Maida, A., et al. (2011). Physiological and pharmacological mechanisms through which the DPP-4 inhibitor sitagliptin regulates glycemia in mice. Endocrinology 152, 3018-3029.

Wichmann, A., Allahyar, A., Greiner, T. U., Plovier, H., Lunden, G. O., Larsson, T., Drucker, D. J., Delzenne, N. M., Cani, P. D., and Backhed, F. (2013). Microbial modulation of energy availability in the colon regulates intestinal transit. Cell Host Microbe 14, 582-590.

Widmann, C., Dolci, W., and Thorens, B. (1997). Internalization and homologous desensitization of the GLP-1 receptor depend on phosphorylation of the receptor carboxyl tail at the same three sites. Mol Endocrinol 11, 1094-1102.

Xu, G., Kaneto, H., Laybutt, D. R., Duvivier-Kali, V. F., Trivedi, N., Suzuma, K., King, G. L., Weir, G. C., and Bonner-Weir, S. (2007). Downregulation of GLP-1 and GIP receptor expression by hyperglycemia: possible contribution to impaired incretin effects in diabetes. Diabetes 56, 1551-1558.

Yang, L., Yao, D., Yang, H., Wei, Y., Peng, Y., Ding, Y., and Shu, L. (2016). Puerarin protects pancreatic beta-cells in obese diabetic mice via activation of GLP-1R signaling. Mol Endocrinol, me20151213.

Yarullina, D. R., Mikheeva, R. O., Sabirullina, G. I., Zelenikhin, P. V., Ilinskaya, O. N., and Sitdikova, G. F. (2016). Role of Nitric Oxide Produced by *Lactobacilli* in Relaxation of Intestinal Smooth Muscles. Bull Exp Biol Med 160, 343-346.

Younan, S. M., and Rashed, L. A. (2007). Impairment of the insulinotropic effect of gastric inhibitory polypeptide (GIP) in obese and diabetic rats is related to the downregulation of its pancreatic receptors. Gen Physiol Biophys 26, 181-193.

The invention claimed is:

1. A method of enhancing the potency of an incretin-based drug administered to a diabetic subject as part of a treatment regimen, wherein the diabetic subject has developed a resistance to the incretin-based drug, the method comprising:
   administering to the diabetic subject a pharmaceutically effective amount of at least one probiotic *Lactobacillus* strain in combination with the incretin-based drug.

2. The method of claim 1 wherein the incretin-based drug is a GLP-1 receptor agonist or a DDP-4 inhibitor.

3. The method of claim 1 wherein the probiotic *Lactobacillus* strain is administered to the subject by ingestion and the incretin-based drug is administered to the subject subcutaneously.

4. The method of claim 1 wherein the probiotic *Lactobacillus* strain is selected from the group consisting of *Lactobacillus acetotolerans, Lactobacillus acidipiscis, Lactobacillus acidophilus, Lactobacillus agilis, Lactobacillus algidus, Lactobacillus alimentarius, Lactobacillus amylolyticus, Lactobacillus amylophilus, Lactobacillus amylovorus, Lactobacillus animalis, Lactobacillus arizonensis, Lactobacillus aviarius, Lactobacillus bifermentans, Lactobacillus brevis, Lactobacillus buchneri, Lactobacillus casei, Lactobacillus coelohominis, Lactobacillus collinoides, Lactobacillus coryniformis* subsp. *coryniformis, Lactobacillus coryniformis* subsp. *torquens, Lactobacillus crispatus, Lactobacillus curvatus, Lactobacillus cypricasei, Lactobacillus delbrueckii* subsp. *bulgaricus, Lactobacillus delbrueckii* subsp *delbrueckii, Lactobacillus delbrueckii* subsp. *lactis, Lactobacillus durianus, Lactobacillus equi, Lactobacillus farciminis, Lactobacillus ferintoshensis, Lactobacillus fermentum, Lactobacillus formicalis, Lactobacillus fructivorans, Lactobacillus frumenti, Lactobacillus fuchuensis, Lactobacillus gallinarum, Lactobacillus gasseri, Lactobacillus graminis, Lactobacillus hamsteri, Lactobacillus helveticus, Lactobacillus helveticus* subsp. *jugurti, Lactobacillus heterohiochii, Lactobacillus hilgardii, Lactobacillus homohiochii, Lactobacillus intestinalis, Lactobacillus japonicus, Lactobacillus jensenii, Lactobacillus johnsonii, Lactobacillus kefiri, Lactobacillus kimchii, Lactobacillus kunkeei, Lactobacillus leichmannii, Lactobacillus letivazi, Lactobacillus lindneri, Lactobacillus malefermentans, Lactobacillus mali, Lactobacillus maltaromicus, Lactobacillus manihotivorans, Lactobacillus mindensis, Lactobacillus mucosae, Lactobacillus murinus, Lactobacillus nagelii, Lactobacillus oris, Lactobacillus panis, Lactobacillus pantheri, Lactobacillus parabuchneri, Lactobacillus paracasei* subsp. *paracasei, Lactobacillus paracasei* subsp. *pseudoplantarum, Lactobacillus paracasei* subsp. *tolerans, Lactobacillus parakefiri, Lactobacillus paralimentarius, Lactobacillus paraplantarum, Lactobacillus pentosus, Lactobacillus perolens, Lactobacillus plantarum, Lactobacillus pontis, Lactobacillus psittaci, Lactobacillus reuteri, Lactobacillus rhamnosus, Lactobacillus ruminis, Lactobacillus sakei, Lactobacillus salivarius, Lactobacillus salivarius* subsp. *salicinius, Lactobacillus salivarius* subsp. *salivarius, Lactobacillus sanfranciscensis, Lactobacillus sharpeae, Lactobacillus suebicus, Lactobacillus thermophilus, Lactobacillus thermotolerans, Lactobacillus vaccinostercus, Lactobacillus vaginalis, Lactobacillus versmoldensis, Lactobacillus vitulinus, Lactobacillus vermiforme*, and *Lactobacillus zeae*.

5. The method of claim 1 wherein the probiotic *Lactobacillus* strain is a food grade bacteria.

6. The method of claim 1 wherein the probiotic *Lactobacillus* strain is encapsulated in order to be protected against the stomach or is administered to the subject in the form of a food composition.

7. The method of claim 2 further comprising administering to the subject a therapeutically effective amount of a drug selected from the group consisting of sulfonylurea drugs, biguanides, alpha-glucosidase inhibitors, thiazolidinediones, and meglitinides.

8. The method of claim 1, wherein the pharmaceutically effective amount is an amount sufficient to reduce insulin resistance in the diabetic subject.

* * * * *